United States Patent
Liu et al.

(10) Patent No.: US 9,599,625 B2
(45) Date of Patent: Mar. 21, 2017

(54) BLOOD BIOMARKER FOR EARLY BLOOD BRAIN BARRIER DISRUPTION IN ISCHEMIC STROKE

(71) Applicants: Ke Jian Liu, Albuquerque, NM (US); Wenlan Liu, Albuquerque, NM (US); Graham Timmins, Albuquerque, NM (US); Rong Pan, Albuquerque, NM (US)

(72) Inventors: Ke Jian Liu, Albuquerque, NM (US); Wenlan Liu, Albuquerque, NM (US); Graham Timmins, Albuquerque, NM (US); Rong Pan, Albuquerque, NM (US)

(73) Assignee: STC.UNM, Albuquerque, NM (US)

(*) Notice: Subject to any disclaimer, the term of this patent is extended or adjusted under 35 U.S.C. 154(b) by 0 days.

(21) Appl. No.: 14/325,126

(22) Filed: Jul. 7, 2014

(65) Prior Publication Data

US 2014/0314737 A1    Oct. 23, 2014

Related U.S. Application Data

(63) Continuation-in-part of application No. 13/660,675, filed on Oct. 25, 2012, now abandoned.

(60) Provisional application No. 61/551,200, filed on Oct. 25, 2011.

(51) Int. Cl.
   *G01N 33/68* (2006.01)

(52) U.S. Cl.
   CPC ... *G01N 33/6893* (2013.01); *G01N 2333/4703* (2013.01); *G01N 2800/2871* (2013.01); *G01N 2800/52* (2013.01)

(58) Field of Classification Search
   None
   See application file for complete search history.

(56) References Cited

U.S. PATENT DOCUMENTS

2015/0198617 A1   7/2015   Liu et al.

OTHER PUBLICATIONS

Van Itallie et al., J. Cell Sci. 110: 1113-1121 (1997).*
Obermaier et al., Nat. Med. 19(12): 1584-1596 (2013).*
American Stroke Association, http://www.strokeassociation.org/STROKEORG/AboutStroke/Treatment/Stroke-Treatments_UCM_310892_Article.jsp#.V1mv-U32bDA, accessed Jun. 9, 2016.*
Alberts. "tPA in acute ischemic stroke: United States experience and issues for the future". *Neurology*. 1 9 9 8 , 51;S53-55.
Amersham, "Quantification of western blots using enhanced chemiluminescence". https://www.gelifesciences.com/genchls_images/GELS/Relate%20Content/Files/131       4729545976/litdoc18114790_20110830214030.pdf, 2000, accessed Oct. 3, 2013.
Andras et al. "HIV-1 Tat protein alters tight junction protein expression and distribution in cultured brain endothelial cells". *J. NeUI-osci Res*. 2003. 74:255-265.
Asahi et al. "Effects of matrix metalloproteinase-9 gene knock-out on the proteolysis of blood-brain barrier and white matter components after cerebral ischemia". *J. Neurosci*. 2001. 21:7724-7732.

(Continued)

*Primary Examiner* — Erin M Bowers
(74) *Attorney, Agent, or Firm* — Mueting, Raasch & Gebhardt, P.A.

(57) ABSTRACT

Methods and apparatus for determining blood brain barrier (BBB) damage and treating patients who may have suffered from BBB damage due to an ischemic event are provided. The methods and apparatus involve detecting the presence of cleaved occludin fragments in a sample of blood. According to some embodiments, the method further provides determining the degree of BBB damage based on the concentration of occludin fragments in the sample. In further embodiments the present disclosure provides kits for detecting the presence of occludin fragments in a blood sample.

1 Claim, 16 Drawing Sheets

(56) References Cited

OTHER PUBLICATIONS

Aviv et al. "Hemorrhagic transformation of ischemic stroke: prediction with CT perfusion". *Radiology*. 2009. 250:867-877.
Bang et al. "Prediction of hemorrhagic transformation after recanalization therapy using T2+-permeability magnetic resonance imaging". *Ann Neurol*. 2007. 62:170-176.
Banks et al. "Passage of Peptides Across the Blood-Brain Barrier: Pathophysiological Perspectives". *Life Sciences*. 1996. 59(23):1923-1943.
Benchenane et al. "Oxygen glucose deprivation switches the transport of tPA across the blood-brain barrier from an LRP-dependent to an increased LRP-independent process". *Stroke*. 2005. 36:1065-1070.
Brown et al. "Potent and selective mechanism-based inhibition of gelatinases". *J. Am. Chem. Soc*. 2000. 122:6799-6800.
Butcher et al. "Correlation between amino acid release and neuropathologic outcome in rat brain following middle cerebral artery occlusion"1990. *Stoke*. 21:1727-1733.
Carpenter et al. "Thrombolytic Therapy for Acute Ischemic Stroke beyond Three Hours". *J. Emerg*. Med:doi:10.1016/j jmermed.2010.1005.1009; 2010.
Chen et al. "Severe blood-brain barrier disruption and surrounding tissue injury". *Stroke*. 2009. 40:e666-674.
Date et al. "Hepatocyte growth factor attenuates cerebral ischemia-induced increase in permeability of the blood-brain barrier and decreases in expression of tight junctional proteins in cerebral vessels". *Neurosci Lett*. 2006. 407:141-145.
DeBecker et al. Migration of culture-expanded human mesenchymal stem cells through bone marrow endothelium is regulated by matrix metalloproteinase-2 and tissue inhibitor of metalloproteinase-3. *Haematologica*. 2007. 92:440-449.
del Zoppo et al. "Ischaemic damage of brain microvessesls: inherent risks for thrombolytic treatment in stroke". *J. Neurol Neurosurg Psychiatry*. 1998. 65:1-9.
del Zoppo et al. "Expansion of the time window for treatment of acute ischemic stroke with intravenous tissue plasminogen activator: a science advisory from the American Heart Associate/American Stroke Associate". *Stroke*. 2009. 40:2945-2948.
Derex. "Intracerebral haemorrhage after thrombolysis for acute ischaemic stroke: an update". *J. Neurol Neurosurg Psychiatry*. 2008. 79:1093-1099.
DiNapoli et al. "Early disruptions of the blood-brain barrier may contribute to exacerbated neuronal damage and prolonged functional recovery following stroke in aged rats". *Neurobiol Aging*. 2008. 29:753-764.
Eckle et al. "A2B adenosine receptor dampens hypoxia-induced vascular leak". *Blood*. 2008. 111:2024-2035.
Elai et al. "Increased Blood-Brain Barrier Permeability and Brain Edema After Focal Cerebral Ischemia Induced by Hyperlipidemia: Role of Lipid Peroxidation and Capain-1/2, Matrix Metalloproteinase-2/9, and RhoA Overactivation". *Stroke*. 2011. 42:3238-3244.
Ellison et al. "Matrix remodeling after stroke. De novo expression of matrix proteins and integrin receptors". *Ann NY Acad Sci*. 1999. 890:204-222.
Floyd. "Neuroinflammatory processes are important in neurodegenerative diseases: an hypothesis to explain the increased formation of reactive oxygen and nitrogen species as major factors involved in neurodegenerative disease development". *Free Radic Biol Med*. 1999. 26:1346-1355.
Forster. "Tight junctions and the modulation of barrier function in disease". *Histochem Cell Biol*. 2008. 130:55-70.
Furuichi et al. "Generation of hydrogen peroxide during brief oxygen-glucose deprivation induces preconditioning neuronal protection in primary cultured neurons". *J. Neurosci Res*. 2005. 79:816-824.
Gasche et al. "Matrix metalloproteinases and diseases of the central nervous system with a special emphasis on ischemic brain". *Front Biosci*. 2006. 11:1289-1301.
Gerriets et al. "Edema formation in the hyperacute phase of ischemic stroke". *J. Neurosurg*. 2009. 111:1036-1042.
Giebel et al. "Matrix metalloproteinases in early diabetic retinopathy and their role in alteration of the blood-retinal barrier". *Lab Invest*. 2005. 85:597-607.
Gong et al. "Inflammatory macrophage migration requires MMP-9 activation by plasminogen in mice". *J. Clin. Invest*. 2008. 118:3012-3024.
Grabovac et al. "Improvement of the intestinal membrane permeability of low molecular weight heparin by complexation with stem bromelain". *Intl. Journal of Pharmaceutics*. 2006. 326:153-159.
Hacke et al. "Thrombolysis with alteplase 3 to 4.5 hours after acute ischemic stroke". *N. Engl J Med*. 2008. 359:1317-1329.
Hallenbeck et al. "Background review and current concepts of reperfusion injury". *Arch Neurol*. 1990. 47:1245-1254.
Hawkins et al. "The blood-brain barrier/neurovascular unit in health and disease". *Pharmacol Rev*. 2005. 57:173-185.
Heo et al. "Matrix metalloproteinases increase very early during experimental focal cerebral ischemia". *J. Cereb Blood Flow Metab*. 1999. 19:624-633.
Hjort et al. "MRI detection of early blood-brain barrier disruption: parenchymal enhancement predicts focal hemorrhagic transformation after thrombolysis". *Stroke*. 2008. 39:1025-1028.
Jin et al. "Molecular insights and therapeutic targets for blood-brain barrier disruption in ischemic stroke: critical role of matrix metalloproteinases and tissue-type plasminogen activator". *Neurobiol Dis*. 2010. 38:376-385.
Jung et al. "Reperfusion and neurovascular dysfunction in stroke: from basic mechanism to potential strategies for neuroprotection". *Molecular Neurobiology*. 2010. 41:172-179.
Kamada et al. "Influence of hyperglycemia on oxidative stress and matrix metalloproteinase-9 activation after focal cerebral ischemia/reperfusion in rats: relation to blood-brain barrier dysfunction". *Stroke*. 2007. 38:1044-1049.
Kassner et al. "Recombinant tissue plasminogen activator increases blood-brain barrier disruption in acute ischemic stroke: an MR imaging permeability study". *AJNR Am J Neuroradiol*. 2009. 30:1864-1869.
Kastrup et al. "Early disruption of the blood-brain barrier after thrombolytic therapy predicts hemorrhage in patients with acute stroke". *Stroke*. 2008. 39:2384-2387.
Kleindorfer et al. "US estimates of recombinant tissue plasminogen activator use: ICD-9 codes substantially underestimate". 2008. *Stroke*. 39:924-928.
Knight et al. "Prediction of impending hemorrhagic transformation in ischemic stroke using magnetic resonance imaging in rats". *Stroke*. 1998. 29:144-151.
Kolev et al. "Matrix metalloproteinase-9 expression in post-hypoxic human brain capillary endothelial cells: H2O2 as a trigger and NF-kappaB as a signal transducer". *Thromb Haemost*. 2003. 90:528-537.
Kondo et al. "Thrombin induces rapid disassembly of claudin-5 from the tight junction of endothelial cells", *Exp Cell Res*. 2009. 315:2879-2887.
Lapchak. "Hemorrhagic transformation following ischemic stroke: significance, causes, and relationship to therapy and treatment". *Curr Neurol Neurosci Rep*. 2002. 2:38-43.
Larson et al. "Endothelial EphA receptor stimulation increases lung vascular permeability". *Am J Physiol Lung Cell Mol Physiol*. 2008. 295 :L431-439.
Latour et al. "Early blood-brain barrier disruption in human focal brain ischemia". *Ann Neurolo*. 2004. 56:468-477.
Lisanti et al. "Caveolae, caveolin and caveolin-rich membrane domains: a signaling hypothesis". *Trends Cell Biol*. 1994. 4:231-235.
Lischper et al. "Metalloproteinase mediated occluding cleavage in the cerebral microcapillary endothelium under pathological conditions". *Brain Res*. 2010. 1326:114-127.
Liu et al. "Matrix meatlloproteinases and free radicals in cerebral ischemia". *Free Radic Biol. Med*. 2005. 39:71-80.
Liu et al. "Hydroxyl radical formation is greater in striatal core than in penumbra in a rat model of ischemic stroke". *J. Neurosci Res*. 71:882-888.

(56) References Cited

OTHER PUBLICATIONS

Liu et al. "normobaric hyperoxia reduces the neurovascular complications associated with delayed tissue plasminogen activator treatment in a rat model of focal cerebral ischemia". *Stroke.* 2009a. 40:2526-2531.

Liu et al. "Normobaric hyperoxia attenuates early blood-brain barrier disruption by inhibiting MMP-9-mediated occluding degradation in focal cerebral ischemia". *J. Neurochem.* 2009b. 108:811-820.

Liu et al. "Normobaric hyperoxia inhibits NADPH oxidase-mediated matrix metalloproteinase-I induction in cerebral microvessels in experimental stroke". *J. Neurochem.* 2008. 107:1196-1205.

Liu et al. "interstitial p)2 in ischemic penumbra and core are differentially affected following transient focal cerebral ischemia in rats". *J. Cereb Blood Flow Metab.* 2004. 24(3):343-349.

Lloyd-Jones et al. Executive summary: heart disease and stroke statistics-2010 update: a report from the American Heart Association. *Circulation* 121:948-954.

Lo et al. "Endothelin-1 overexpression leads to further water accumulation and brain edema after middle cerebral artery occlusion via aquaporin 4 expression in astrocytic end-feet". *J. Cereb blood Flow Metab.* 2005. 25:998-1011.

Mattila et al. "Cerebral mast cells mediate blood-brain barrier disruption in acute experimental ischemic stroke through perivascular gelatinase activation". *Stroke.* 2011. 42:3600-3605.

McCaffrey et al. "Tight junctions contain oligomeric protein assembly critical for maintaining blood-brain barrier integrity in vivo". *Journ of Neurochemistry.* 2007. 103:2540-2555.

McColl et al. "Systemic inflammation alters the kinetics of cerebrovascular tight junction disruption after experimental stroke in mice". *J. Neurosci.* 2008. 28:9451-9462.

Min et al. "2-Methoxy-2,4-diphenyl-3(2H)-furanone-labeled gelatin zymography and reverse zymography: a rapid real time method for quantification of matrix metalloproteinases-2 and -9 and tissue inhibitors of metalloproteinases". *Electrophoresis.* 2006. 27:357-364.

Nag et al. "Increased caveolin-1 expression precedes decreased expression of occluding and claudin-5 during blood-brain barrier breakdown". *Acta Neuropathol.* 2007. 114:459-469.

Nagaraja et al. "MRI and quantitative autoradiographic studies following bolus injections of unlabeled and (14) C-labeled gadolinium-diethylenetriaminepentaacetic acid in a rat model of stroke yield similar distribution volumes and blood-to-brain influx rate constants". *MNR Biomed.* 2011. 24:547-558.

Nakamuta et al. "Effects of fibril—or fixed-collagen on matrix metalloproteinase-1 and tissue inhibitor of matrix metalloproteinase-1 production in the human hepatocyte cell line HLE". *Word J Gastroenterol.* 2005. 11:2264-2268.

Nilsson et al. "Estradiol and tamoxifen regulate endostatin generation via matrix metalloproteinase activity in breast cancer in vivo". *Cancer Res.* 2006. 66:4789-4794.

Ninds. "The Ninds t-PA stroke Study Group. Intracerebral hemorrhage after intravenous t-PA therapy for ischemic stroke". *Stoke.* 1997. 28:2109-2118.

Okamoto et al. "Caveolins, a family of scaffolding proteins for organizing "preassembled signaling complexes" at the plasma membrane". *J. Biol Chem.* 1998. 273:5419-5422.

Romanic et al. "Matrix metalloproteinase expression increases after cerebral focal ischemia in rats: inhibition of matrix metalloproteinase-9 reduces infarct size". *Stroke.* 1998. 19:1020-1030.

Rosenberg et al. "Matrix metalloproteinases in neuroinflammation and cerebral ischemia". *Ernst Schering Res Found Workshop.* 2004. 1-16.

Rosenberg et al. "Matrix metalloproteinases and TIMPs are associated with blood-brain barrier opening after reperfusion in rate brain". *Stroke.* 1998. 29:2189-2195.

Sbai et al. "Differential vesicular distribution and trafficking of MMP-2, MMP-9, and their inhibitors in astrocytes". *Glia.* 2010. 58:344-366.

Sbai et al. "Vesicular trafficking and secretion of matrix metalloproteinases-2, -9 and tissue inhibitor of metalloproteinases-1 in neuronal cells". *Mol Cell Neurosci.* 2008. 39:549-568.

Schnaeker et al. "Microtubule-dependent matrix metalloproteinase-2/matrix metalloproteinase-9 exocytosis: prerequisite in human melanoma cell invasion". *Cancer Res.* 2004. 64:8924-8931.

Simard et al. Brain oedema in focal ischaemia: molecular pathophysiology and theoretical implications. *Lancet Neurol.* 2007. 6:258-268.

Slevin et al. "Identification of pro-angiogenic markers in blood vessels from stroked-affected brain tissue using laser-capture microdissection". *BMC Genomics.* 2009. 10:113.

Smart et al. "Caveolins, liquid-ordered domains, and signal transduction". *Mol Cell Biol.* 1999. 19:7289-7304.

Song et al. "Inhibition of tumor angiogenesis in vivo by a monoclonal antibody targeted to domain 5 of high molecular weight kininogen". *Blood.* 2004. 104(7):2065-2072.

Song et al. "Caveolin-1 regulates expression of junction-associated proteins in brain microvascular endothelial cells". *Blood.* 2007. 109:1515-1523.

Stamatovic et al. "Caveolae-mediated internalization of occluding and claudin-5 during CCL2-induced tight junction remodeling in brain endothelial cells". *J Biol Chem.* 2009. 284:19053-19066.

Sun et al. "Oxygen therapy reduces secondary hemorrhage after thrombolysis in thromboembolic cerebral Ischemia". *J Cereb Blood Flow Metab.* 2010. 30:1651-1660.

Tanne. "Imaging blood-brain barrier disruption: an evolving tool for assessing the risk of hemorrhage after thrombolysis". *Nat Clin Pract Neurol.* 2008. 4:644-645.

Tanne et al. "Markers of increased risk of intracerebral hemorrhage after intravenous recombinant tissue plasminogen activator therapy for acute ischemic stroke in clinical practice: the Multicenter rt-PA Stroke Survey". *Circulation* 2005. 105:1679-1685.

Taraboletti et al. "Bioavailability of VEGF in tumor-shed vesicles depends on vesicle burst induced by acidic pH". *Neoplasia.* 2006. 8:96-103.

Tokunaga et al. "A Novel Monoclonal Antibody Against the Second Extracellular Loop of Occludin Disrupts Epithelial Cell Polarity". *J. Histochem. Cytochem.* 2007. 55(7):735-744.

Vorbrodt et al. "Molecular anatomy of interendothelial junctions in human blood-brain barrier microvessels". *Folia Histochem Cytobiol.* 2004. 42::67-75.

Wang. "Triggers and mediators of hemorrhagic transformation in cerebral ischemia". *Mol Neurobiol.* 2003. 28:229-244.

Wang et al. "Lipoprotein receptor-mediated induction of matrix metalloproteinase by tissue plasminogen activator". *Nat Med.* 2003. 9:1313-1317.

Wang et al. "Detectionof in vivo matrix metalloproteinase activity using microdialysis sampling and liquid chromatography/mass spectrometry". *Anal Chem.* 2009. 81:9961-9971.

Wang et al. "Valproic acid attenuates blood-brain barrier disruption in a rat model of transient foal cerebral Ischemia: the roles of HDAC and MMP-9 inhibition". *J Cereb Blood Flow Metab.* 2011. 31:52-57.

Warach et al. "Evidence of reperfusion injury, exacerbated by thrombolytic therapy, in human focal brain ischemia using a novel imaging marker of early blood-brain barrier disruption". *Stroke.* 2004. 35:2659-2661.

Wen et al. "Opposite action of peroxisome proliferator-activated receptor-[gamma] in regulating renal inflammation: functional switch by its ligand". *J. Biol Chem.* 2010.

Wolburg et al. "Tight junctions of blood-brain barrier: development, composition and regulation". *Vascul Pharmacol.* 2002. 38:323-337.

Yang et al. "Agmatine inhibits matrix metalloproteinase-9 via endothelial nitric oxide synthase in cerebral endothelial cells". *Neurol Res.* 2007a. 29:749-754.

Yang et al. "Matrix metalloproteinase-mediated disruption of tight junction proteins in cerebral vessels is reversed by synthetic matrix metalloproteinase inhibitor in focal ischemia in rat". *J. Cereb. Blood Flow Metab.* 2007. 27:697-709.

Yepes et al. "Tissue-type plasminogen activator induces opening of the blood-brain barrier via the LDL receptor-related protein". *J Clin Invest.* 2003. 112:1533-1540.

(56) References Cited

OTHER PUBLICATIONS

Yuan et al. "Normobaric hyperoxia delays and attenuates early nitric oxide production in focal cerebral ischemic rats". *Brain Res.* 2010. 1352:248-254.

Yong et al. "Matrix metalloproteinases and diseases of the CNS". *Trends Neurosci.* 1998. 21:75-80.

Zehendner et al. "Capase-3 contributes to ZO-1 and C1-5 right junction disruption in rapid anoxic neurovascular unit damage". *PLoS One.* 2011. 6:e16760.

Zhang et al. "Microglial low-density lipoprotein receptor-related protein 1 mediates the effect of tissue-type plasminogen activator on matrix metalloproteinase-9 activity in the ischemic brain". *J. Cereb Blood Flow Metab.* 2009. 29:1946-1954.

Zhu et al. "Protein S controls hypoxic/ischemic blood-brain barrier disruption through the TAM receptor Tyro3 and sphingosine 1-phosphate receptor". *Blood.* 2010. 115:4963-4972.

Zozulya et al. "Pericyte-endothelial cell interaction increases MMP-9 secretion at the blood-brain barrier in vitro". *Brain Res.* 2008. 1189:1-11.

* cited by examiner

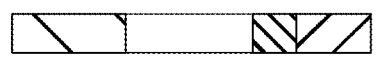
FIG. 5
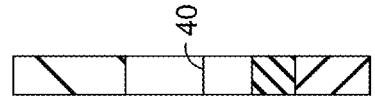
FIG. 10
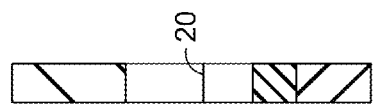
FIG. 4
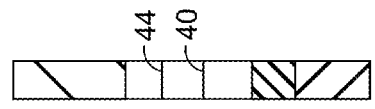
FIG. 9
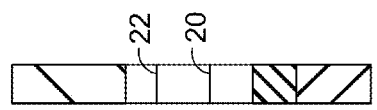
FIG. 3
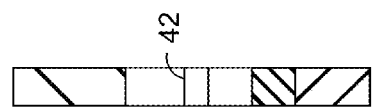
FIG. 8
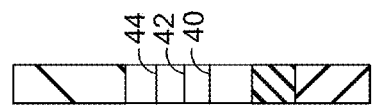
FIG. 2
FIG. 7
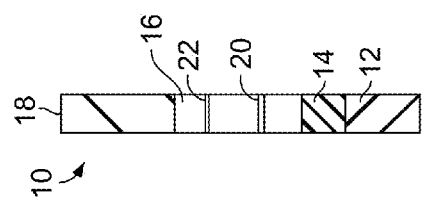
FIG. 1
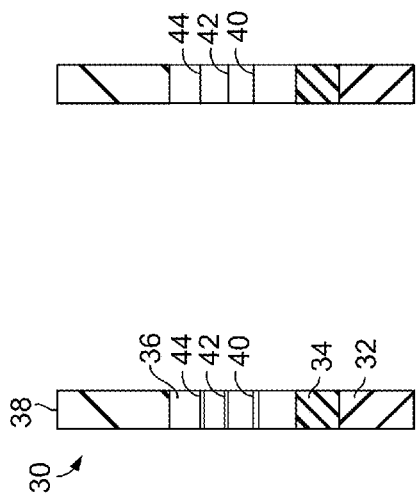
FIG. 6

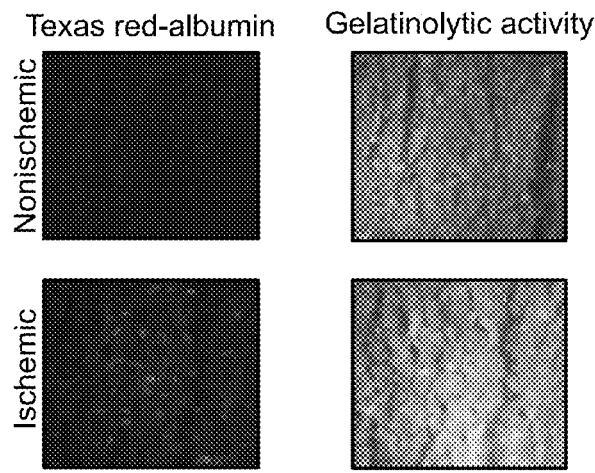
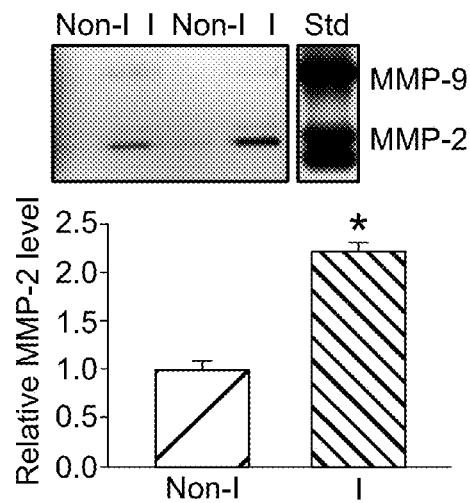
FIG. 29
FIG. 30
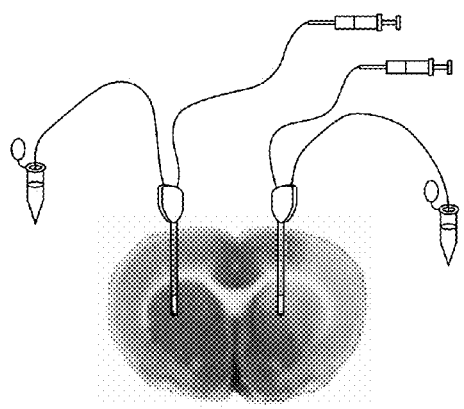
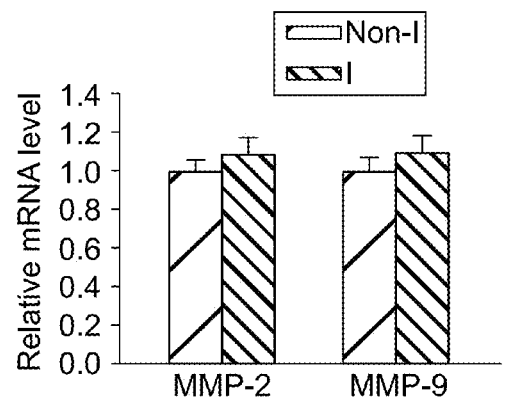
FIG. 31
FIG. 32

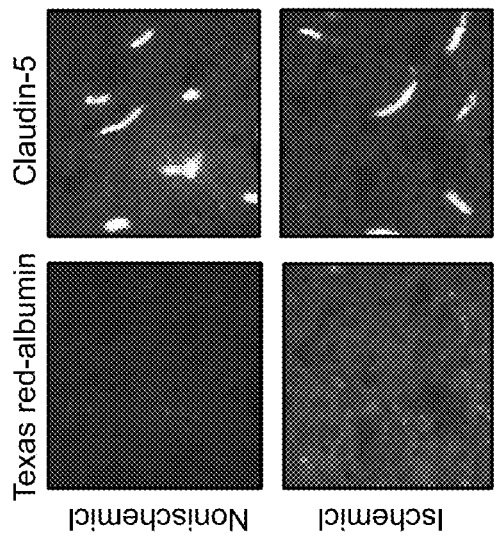
FIG. 33
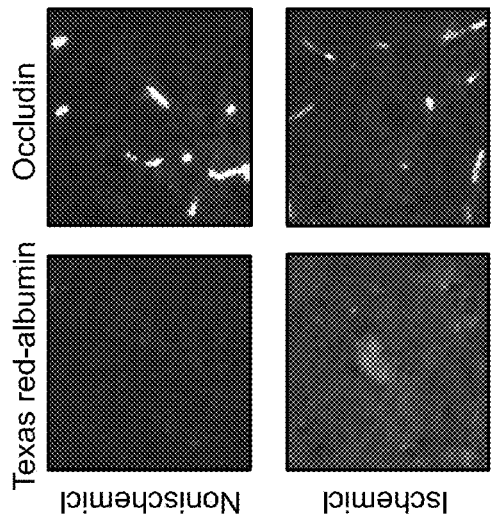
FIG. 34
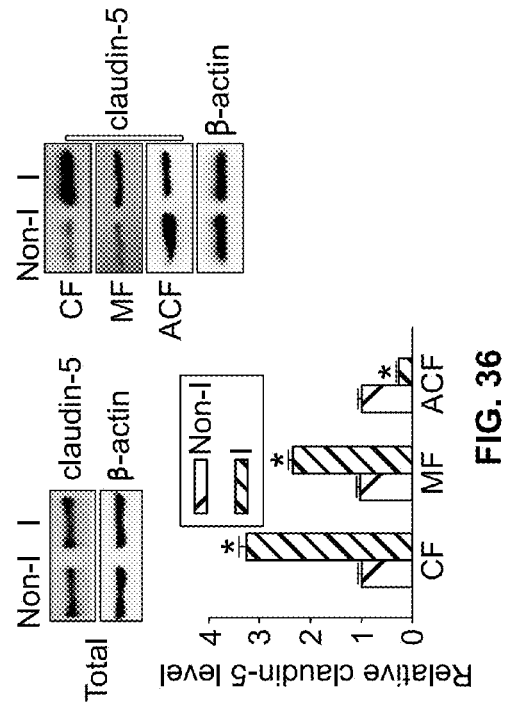
FIG. 35
FIG. 36
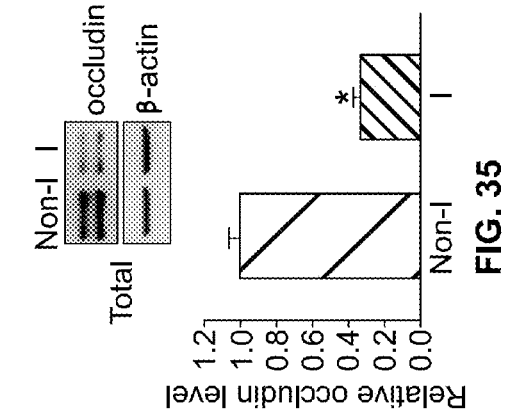

BLOOD BIOMARKER FOR EARLY BLOOD BRAIN BARRIER DISRUPTION IN ISCHEMIC STROKE

CROSS-REFERENCE TO RELATED APPLICATIONS

The following application is a continuation-in-part of currently pending U.S. application Ser. No. 13/660,675, filed Oct. 25, 2012, which claims benefit of U.S. Provisional Application No. 61/551,200, filed Oct. 25, 2011, each of which is hereby incorporated by reference in its entirety.

SEQUENCE LISTING

A sequence listing was submitted via EFS with the present application and is hereby incorporated by reference. The text file is named "2012-035-03_7140203_Seq_Lis_ST25," was created Jul. 7, 2014, and is 18 KB. The compliant ASCII text file submitted via EFS is considered under 37 CFR 1.821 (c) and 37 CFR 1.821 (e) to be sufficient to satisfy the requirements of submitting both paper and electronic sequence listings.

BACKGROUND

Stroke is the third leading cause of death and the leading cause of adult disability in developed countries. In the United States, approximately 795,000 people experience a new or recurrent each year. See, e.g, Lloyd-Jones et al., Executive summary: heart disease and stroke statistics—2010 update: a report from the American Heart Association. Circulation 121:948-954; 2010. Intravenous thrombolysis with tissue plasminogen activator (tPA) remains the only FDA-approved therapy for acute ischemic stroke. At present, only a small fraction of potentially eligible stroke patients in the United States are receiving tPA therapy, and it is estimated that the rate of tPA use is 1.8% to 2.1% of all ischemic stroke patients. See e.g., Kleindorfer et al., US estimates of recombinant tissue plasminogen activator use: ICD-9 codes substantially underestimate. Stroke 39:924-928; 2008. One barrier to widespread implementation of acute stroke thrombolysis is the fear of symptomatic intracerebral hemorrhage (ICH). See, Tanne et al., Markers of increased risk of intracerebral hemorrhage after intravenous recombinant tissue plasminogen activator therapy for acute ischemic stroke in clinical practice: the Multicenter rt-PA Stroke Survey. Circulation 105:1679-1685; 2002. Evidence from randomized clinical trials and subsequent clinical experience clearly demonstrates that tPA thrombolysis presents real safety concerns due to a 10-fold increase in the incidence of symptomatic ICH and a 50% mortality rate in stroke patients who have such bleeding. See, e.g., NINDS. The NINDS t-PA Stroke Study Group. Intracerebral hemorrhage after intravenous t-PA therapy for ischemic stroke. Stroke 28:2109-2118; 1997; Lapchak, P. A. Hemorrhagic transformation following ischemic stroke: significance, causes, and relationship to therapy and treatment. Curr Neurol Neurosci Rep 2:38-43; 2002; and Carpenter, C. R. et al., Thrombolytic Therapy for Acute Ischemic Stroke beyond Three Hours. J Emerg Med:doi:10.1016/j.jmermed.2010.1005.1009; 2010.

There has been an urgent need to identify early diagnostic indicators to exclude "eligible patients" (within the 3-hr thrombolytic time window) at high risk of ICH and to include "non-eligible patients" (beyond the 3-hr limit, but still presenting salvageable penumbral tissue, but at low risk of ICH) for tPA treatment, thus allowing more stroke patients to benefit from tPA treatment. Unfortunately, there are currently no such early indicators for ICH available to guide tPA thrombolysis in clinical practice.

Blood brain barrier (BBB) disruption is a hypothesized precursor to ICH and the timing of BBB damage is early enough to be within the thrombolytic time window. See, Warach, S. et al., Evidence of reperfusion injury, exacerbated by thrombolytic therapy, in human focal brain ischemia using a novel imaging marker of early blood-brain barrier disruption. Stroke 35:2659-2661; 2004; and Hacke, W. et al., Thrombolysis with alteplase 3 to 4.5 hours after acute ischemic stroke. N Engl J Med 359:1317-1329; 2008.

Using advanced permeability MRI techniques, a causal predictive relationship between early ischemic BBB damage and tPA-associated ICH has been supported by animal and human stroke studies. See NINDS and Warach et al, cited above, as well as Knight, R. A. et al., Prediction of impending hemorrhagic transformation in ischemic stroke using magnetic resonance imaging in rats. Stroke 29:144-151; 1998; Sun, L. et al., Oxygen therapy reduces secondary hemorrhage after thrombolysis in thromboembolic cerebral ischemia. J. Cereb. Blood Flow Metab; Kassner, A. et al., Recombinant tissue plasminogen activator increases blood-brain barrier disruption in acute ischemic stroke: an MR imaging permeability study. AJNR Am J Neuroradiol 30:1864-1869; 2009; and Hjort, N. et al., MRI detection of early blood-brain barrier disruption: parenchymal enhancement predicts focal hemorrhagic transformation after thrombolysis. Stroke 39:1025-1028; 2008. These studies all showed an intriguing phenomenon that ischemic brain regions with compromised BBB at the time of tPA administration are at high risk of intracerebral bleeding at later times during thrombolytic reperfusion. As thus, early ischemic BBB damage appears to be a key factor to determine whether ischemic brain tissue can safely withstand a return of blood flow and is increasingly considered a promising pretreatment predictor for post-thrombolysis ICH. Currently, great efforts have been made to develop a BBB damage-based MRI signature to predict post-thrombolysis ICH and these efforts have achieved substantial progress. However, it may not be practical to use this MRI signature as an early indicator for ICH because quantitative MRI measurement for BBB permeability takes time (at least 1 hr or longer), while in acute stroke care, every minute counts as ischemic brain tissue dies fast. In addition, limited access, high cost and low sensitivity are added concerns to MRI measurement. In contrast, a rapid and reliable blood-test based indicator for early ischemic BBB damage would be an ideal predictor of post-thrombolysis ICH. In addition to helping triage stroke patients for thrombolytic therapy, a biomarker for early BBB damage may help guide the delivery of neuroprotectants to the brain to reap their maximum benefit because most neuroprotectants cannot cross the BBB or are incapable of timely reaching their desired sites of action. Early BBB damage is also a common event contributing to brain injury and worse outcome in patients with traumatic brain injury, thus a quick diagnostic biomarker of BBB damage may also help improve the management of traumatic brain injury.

SUMMARY

Methods and apparatus for determining blood brain barrier (BBB) damage are provided. The method comprises detecting the presence of occludin fragments in a blood sample. According to some embodiments, the method further provides determining the degree of BBB damage based on the concentration of occludin fragments in the sample. According to still further embodiments, the method further provides determining whether an ischemic event has occurred and measuring the amount of time that has passed since the ischemic event occurred. In further embodiments the present disclosure provides a kit for detecting the presence of occludin fragments in a blood sample.

BRIEF DESCRIPTION OF THE DRAWINGS

FIG. 1 is schematic illustration of an exemplary test strip assay for the presence of occludin fragments in a sample according to an embodiment of the present disclosure.

FIG. 2 depicts the test strip of FIG. 1 presenting a result that is positive for the presence of occludin fragments in the sample.

FIG. 3 depicts the test strip of FIG. 1 presenting a negative result.

FIG. 4 depicts the test strip of FIG. 1 presenting an invalid result.

FIG. 5 depicts the test strip of FIG. 1 presenting an invalid result.

FIG. 6 is a schematic illustration of another exemplary test strip assay for the presence of occludin fragments in a sample according to another embodiment of the present disclosure.

FIG. 7 depicts the test strip of FIG. 6 presenting a result that is positive for the presence of occludin fragments in the sample.

FIG. 8 depicts the test strip of FIG. 6 presenting a result that is positive for the presence of occludin fragments in the sample.

FIG. 9 depicts the test strip of FIG. 6 presenting a negative result.

FIG. 10 depicts the test strip of FIG. 6 presenting a negative result.

FIG. 29 depicts the results of in situ zymography performed on cryosections obtained from brain tissue injected with Texas Red-albumin. Increased gelatinolytic activity of MMP-2/9 was found in the ischemic striatal tissue (bright green fluorescence), where Texas Red-albumin leakage concurrently occurred. No tracer leakage and weak gelatinolytic activity were seen in the corresponding nonischemic striatal tissue. Scale bar, 50p.m. Experiments were repeated four times with similar results.

FIG. 30 is gel gelatin zymography analysis of collected dialysates showing that MMP-2/9, particularly MMP-2, were significantly increased in the interstitial space of the ischemic striatum. *$p<0.05$ versus Non-I, Student's t test; n=4.

FIG. 31 is a schematic diagram of in vivo microdialysis sampling, by which MMP-2/9 in the interstitial space of the nonischemic (Non-I) and ischemic (I) striatum were collected during 2 h MCAO.

FIG. 32 is a graph showing that MMP-2/9 mRNA expression was not changed in the ischemic striatal tissue after 2 h MCAO (n=6). Total RNA was extracted from nonischemic and ischemic striatal tissues and mRNA expression was analyzed by real-time RT-PCR. Error bars indicate SEM.

FIG. 33 shows the results of immunostaining for occludin performed on cryosections obtained from brain tissue injected with Texas Red-albumin. Immunostaining (green) for occludin were clearly seen on the microvessels of the nonischemic tissue, where no Texas Red-albumin leakage was observed. In the ischemic hemisphere, tracer leakage was accompanied by reduced occludin staining on the microvessels. Scale bar, 25 μm. Experiments were repeated four times with similar results.

FIG. 34 shows the results of immunostaining for claudin-5 performed on cryosections obtained from brain tissue injected with Texas Red-albumin. Immunostaining (green) for claudin-5 were clearly seen on the microvessels of the nonischemic tissue, where no Texas Red-albumin leakage was observed. In the ischemic hemisphere, tracer leakage was accompanied by no appreciable changes for claudin-5 staining. Scale bar, 25 μm. Experiments were repeated four times with similar results.

FIG. 35 shows Western blot analysis of cerebral microvessels isolated from nonischemic (Non-I) and ischemic (I) hemispheric tissue after 2 h MCAO. Total microvascular extracts and subcellular fractions were prepared for analyzing occludin protein levels with Western blot. As a loading control, the blots were stripped and reprobed with β-actin antibody. MCAO induced a significant reduction in occludin levels in total microvascular extracts. *$p<0.05$ versus Non-I, Student's t test; n=6. Error bars indicate SEM.

FIG. 36 shows Western blot analysis of cerebral microvessels isolated from nonischemic (Non-I) and ischemic (I) hemispheric tissue after 2 h MCAO. Total microvascular extracts and subcellular fractions were prepared for analyzing claudin-5 protein levels with Western blot. As a loading control, the blots were stripped and reprobed with β-actin antibody. MCAO did not change total claudin-5 levels in cerebral microvascular extracts (top left panel) but led to a remarkable reduction in claudin-5 level in the ACF and its significant increases in the CF and MF (top right and bottom panels). *$p<0.05$ versus Non-I, Student's t test; n=4. Error bars indicate SEM.

DETAILED DESCRIPTION

According to an embodiment the present disclosure provides quick and reliable methods for diagnosing blood brain barrier (BBB) disruption. Such diagnosis may, for example, provide a biomarker for assessing the risk of post-thrombolysis ICH and guiding treatment decisions.

Figure 37:
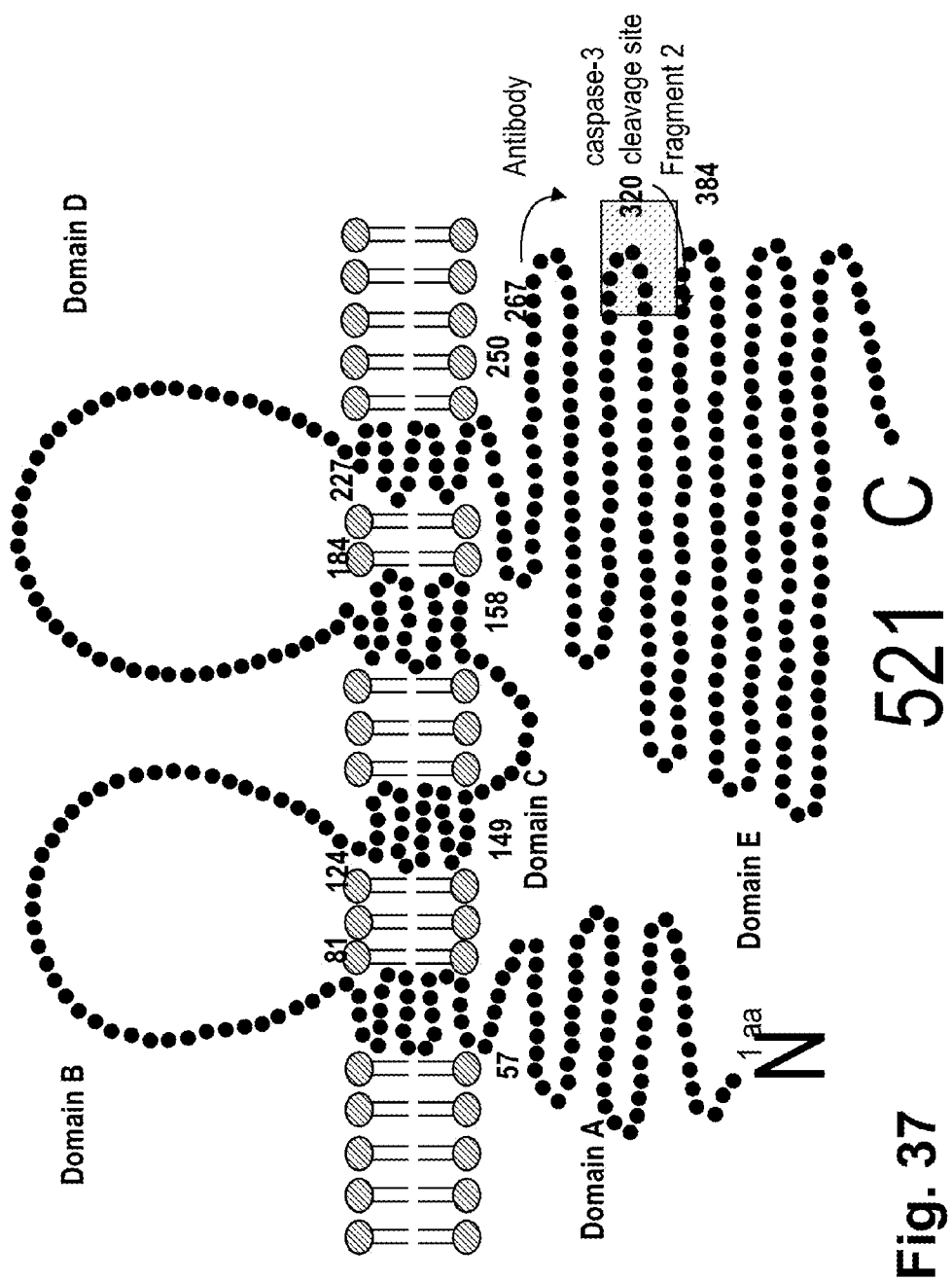
FIG. 37 is a depiction of the transmembrane protein Occludin.

Tight junction proteins form the key structural components of the BBB (i.e. tight junctions) which seal the gaps between adjacent capillary endothelial cells. See e.g., Hawkins, B. T. et al., The blood-brain barrier/neurovascular unit in health and disease. Pharmacol Rev 57:173-185; 2005. Loss of or alterations in tight junction proteins invariably leads to BBB compromisation under ischemic stroke conditions. In particular, occludin is readily degraded into low molecular fragments by matrix metalloproteinases (MMPs) in cerebral ischemia and reperfusion. See e.g., Yang, Y. et al., Matrix metalloproteinase-mediated disruption of tight junction proteins in cerebral vessels is reversed by synthetic matrix metalloproteinase inhibitor in focal ischemia in rat. J Cereb Blood Flow Metab. 27:697-709; 2007. Occludin, a schematic illustration of which is shown in FIG. 37 is a 521 amino acid transmembrane protein in rat and a 523 amino acid transmembrane protein in human. The sequence for the entire rat protein is provided in SEQ. ID NO. 17, while the sequence for the human protein is provided in SEQ ID No. 16. In general, the rat and human proteins share 92% homology. Our recent experiments showed that the tight junction protein occludin is rapidly degraded after ischemia onset (i.e., within 2 hours), contributing to early BBB disruption. Furthermore, cleavage of this protein results in the release of cleaved fragments into the circulating blood stream. We have identified two particular rat occludin fragments which are released into the blood stream, which can be detected, and the presence of which in the blood stream after an ischemic event is able to provide an indication of the occurance of an ischemic event, the time passage since the ischemic event (Fragment 1), and the degree of BBB disruption (Fragment 2). Based on molecular weight, these fragments are believed to be amino acids 120-521 of rat occludin (referred to herein as SEQ ID. NO:18 (also referred to herein as "Fragment 1"): GYGYGYGYGG YTD-PRAAKGF LLAMAAFCFI ASLVIFVTSV IRSGMSRTRR YYLIVIIVSA ILGIMVFIAT IVYIMGVNPT AQASGSMYGS QIYTICSQFY TPGGTGLYVD QYLY-HYCVVD PQEAIAIVLG FMIIVAFALI IVFAVKTRRK MDRYDKSNIL WDKEHIYDEQ PPNVEEWVKN VSAGTQDMPP PPSDYAERVD SPMAYSSNGK VNG-KRSYPDS LYKSPPLVPE VAQEIPLTLS VDDFRQPRYS SNDNLETPSK RTPTKGKAGK AKRTDPDHYE TDYT-TGGESC DELEEDWLRE YPPITSDQQR QLYKRNFDAG LQEYKSLLAE LDEVNKELSR LDRELDDYRE ESEEYMAAAD EYNRLKQVKG SADYKSKKNY CKQLKSKLSH IKRMVGDYDR RKT; and amino acids 320-521 of rat occludin (referred to herein as SEQ ID. NO:19 (also referred to herein as "Fragment 2"): SPMAYSSNGK VNGKRSYPDS LYKSPPLVPE VAQEI-PLTLS VDDFRQPRYS SNDNLETPSK RTPTKGKAGK AKRTDPDHYE TDYTTGGESC DELEEDWLRE YPPITSDQQR QLYKRNFDAG LQEYKSLLAE LDEVN-KELSR LDRELDDYRE ESEEYMAAAD EYN-RLKQVKG SADYKSKKNY CKQLKSKLSH IKRM-VGDYDR RKT.

Furthermore, we have demonstrated that severe BBB damage leads to increased cleavage of occludin, resulting in higher concentrations of detectable occludin fragments in the blood stream and increased loss of occludin in the brain and associated microvessels.

Furthermore, additional experiments, as detailed in the Experimental section below, have shown that after an ischemic event, the concentration of fragment 2 in a patient's circulating blood is strongly correlated with the degree of BBB damage and, rather surprisingly, that the concentration of fragment 2 appears to spike in correlation with the degree of BBB damage that would indicate that a patient is no longer a suitable candidate for tPA treatment, thereby enabling a rapid and relatively inexpensive test for determining whether a particular patient is a suitable candidate for tPA treatment. Furthermore, and also surprisingly, the concentration of fragment 1 in a patient's circulating blood after an ischemic event appears to steadily increase over time, for a period of at least 24 hours, enabling, for example, a rapid and relatively inexpensive test for determining whether and when an ischemic event occurred.

These results are particularly surprising when compared to the results of similar experiments performed on another tight junction protein, Claudin-5, and a protease that degrades tight junction proteins, MMP-9. One would expect to find increased levels of both Claudin-5 and MMP-9 after an ischemic event. However, our experiments did not show such increases and were unable to demonstrate any correlation between the presence of levels of Claudin-5 or MMP-9 in the blood stream with BBB damage.

Accordingly, detection of the presence and/or concentration of cleaved occludin fragments in blood samples provides a quick and reliable method for diagnosing BBB disruption, ischemic events, and/or determining the timing thereof in patients. According to one example, detection of the presence of one or more types of occludin fragments in the blood stream provides a biomarker for assessing the risk of post-thrombolysis ICH and can guide treatment decisions for stroke patients or individuals with other pathological conditions where detection of BBB damage may be important.

The present disclosure thus provides both a method and apparatus for diagnosing BBB disruption, ischemic events, and/or determining the timing based upon detecting the presence and/or concentration of occludin fragments in a blood sample.

Furthermore, according to some embodiments, the disclosure provides a method and apparatus for determining whether or not an acute ischemic stroke patient is a suitable candidate for tPA therapy.

According to an embodiment, the method comprises obtaining a blood sample from a patient and determining if the blood sample contains occludin fragments. According to a further embodiment, the method comprises determining that the patient is not a suitable candidate for tPA therapy if occludin fragments are found within the blood sample. According to a still further embodiment, the method comprises determining that the patient is not a suitable candidate for tPA therapy if the concentration of occludin fragments is above a predetermined threshold.

According to some embodiments, the occludin fragments may comprise or consist of some or all of fragment 1 or the equivalent portion of human occludin or occludin from another species. Alternatively or additionally, the occludin fragments may comprise or consist of some or all of fragment 2 or the equivalent portion of human occludin or occludin from another species. According to some embodiments, the occludin fragment may comprise or consist of the sequences STLAWDRAYGTGIFGGSMNYPYGSGFG-SYGGGFGGYGYGYGYGYGGYTDPRAAK (SEQ ID. 1) or NPTAQASGSMYGSQIYTICSQFYTPGGTGLY-VDQYL YHYCVVDP (SEQ ID 2).

According to one embodiment, the determination of whether the blood sample contains occludin fragments may be performed by exposing the blood sample to an occludin fragment-specific binding partner (OFBP) under suitable conditions that binding between the occludin-fragment and the OFBP can be detected. According to some embodiments, the OFBP may be an antibody, protein, or other molecule that specifically binds one or more fragments of the occludin protein. According to another specific embodiment, the OFBP may be an antibody, protein, or other molecule that specifically binds to at least a portion of amino acids 120-521 of rat occludin (or the equivalent portion of occludin in human or another species). According to a still more specific embodiment, the OFBP may be an antibody, protein, or other molecule that specifically binds to at least a portion of the sequences STLAWDRAYGTGIFGGSMNYPYGS- GFGSYGGGFGGYGYGYGYGYGGYTDPRAAK (SEQ ID NO:1). According to another specific embodiment, the OFBP may be an antibody, protein, or other molecule that specifically binds to at least a portion of amino acids 320-521 of rat occludin (or the equivalent portion of occludin in human or another species.) According to a still more specific embodiment, the OFBP may be an antibody, protein, or other molecule that specifically binds to at least a portion of NPTAQASGSMYGSQIYTICSQFYTPGGTGLYVDQY-LYHYCVVDP (SEQ ID NO:2). According to an even more specific embodiment, the OFBP may be an antibody, protein, or other molecule that specifically and exclusively binds to at least a portion of fragment 1, fragment 2, SEQ ID No: 1 or SEQ ID NO: 2. According to a still further specific embodiment, the OFBP may be an antibody, protein, or other molecule that specifically and exclusively binds only to one of fragment 1, fragment 2, SEQ ID NO; 1, or SEQ ID NO 2. According to another specific embodiment, the OFBP may be an antibody, protein, or other molecule that binds to the entirety of one of fragment 1, fragment 2, SEQ ID NO; 1, or SEQ ID NO 2. According to yet another embodiment the OFBP binds to the caspase-3 cleavage site DYVERVD$^{320}$SPMAY (SEQ ID NO.:15) of occludin. Examples of suitable OFBPs include, but are not limited to mouse anti-human occludin monoclonal antibodies. We have found an antibody that is raised against amino acids 267-518 of rat occludin, and thus including the caspase-3 cleavage site to be a suitable antibody for detecting the presence and concentration of fragment 2 in rat blood. Accordingly, it is believed that a similar antibody raised against the same areas of human (or other species) occludin would be a suitable antibody for detecting the presence and concentration of occludin.

According to an embodiment, occludin fragments in the blood sample can be immunopreciptated using a specific antibody and then detected via western blot and/or enzyme-linked immunosorbent assay (ELISA). Alternatively, other methodologies such as radioimmunoassay and radioimmunoprecipitation assays may be utilized. According to a still further embodiment, the concentration of occludin within the blood sample can be determined by western blot, ELISA, and/or MALDI-TOF MS analyses.

According to a further embodiment, the present disclosure provides a kit for determining whether or not a blood sample contains occludin fragments. In general, the kit contains one or more types of OFBPs, and a mechanism for detecting binding between the OFBPs and occludin fragments in the blood sample. The kit may further contain a mechanism for determining the concentration of occludin fragments in the blood sample. According to some embodiments the OFBPs may be bound to a substrate. According to alternate embodiments, the OFBPs may be in solution, or maintained in another from which may then be solubilized. According to some embodiments, the OFBPs may be designed in such a way that formation of OFBP-occludin fragment complex results in a detectable change (i.e. increase or decrease) in the detectable label. For example, the OFBPs may be designed to bind or otherwise associate with a detectable label, the detectable activity of which is different when bound to or otherwise associated with the OFBP as compared to when it is unbound or otherwise unassociated with the OFBP and which is displaced or otherwise unassociated with the OFBP upon formation of the OFBP-occludin fragment complex. For example, those of skill in the art will be familiar with a wide variety of antibody-ligand-fluorescent label-based detection systems that could be used in such a situation.

According to some embodiment, some of the elements of the kit may be provided in a self-contained test strip similar to the test strips used for pregnancy or other self-administrable tests. In this case, the OFBP may be bound to or otherwise associated with the test strip which may, for example, comprise a capillary membrane configured to draw the blood sample along the test strip through different functional zones. Suitable zones might include a reaction zone, and a detection zone. In this example, the reaction zone would be an area in which the OFBP is allowed to form a complex with occludin fragments in the blood sample, the detection zone would be an area in which the presence of the formed complex causes some detectable reaction—for example, the release of a dye. Some embodiments may include a control zone which enables a user to determine that the test strip is working properly.

An example of a test strip based detection system is shown in FIG. 1. As shown, the test strip 10 includes a sample pad 12, a conjugate pad 14, a membrane 16, and an absorption pad 18. Membrane 16 further includes a test line 20 and a control line 22. According to a specific embodiment, colored colloidal-gold conjugated to a first mouse anti-human antibody against human occludin (AB1) are localized to conjugate pad 14. Membrane 16 defines a test zone wherein a second mouse anti-human antibody against human occludin (AB2) is immobilized at test line 20 and goat anti-mouse IgG antibody is immobilized at control line 22. In use, a sample from the patient which is suspected to contain occludin fragments due to BBB disruption, such as a prepared or unprepared blood or spinal fluid sample is delivered to the sample pad. The fluid is then moved, via capillary action through the conjugate pad, wherein the gold conjugated AB1 is dissolved in the fluid sample and moved to the test zone. If the test sample contains occludin fragments, the occludin fragments will first bind to the gold conjugated AB1 and then to the immobilized AB2, resulting in colorization of test line 20. Excess dissolved AB1 is then trapped by the goat anti-mouse IgG antibody at control line 22, resulting in colorization of test line 22. Accordingly, the presence of color at both the test and control lines, as shown in FIG. 2 indicates a positive presence of occludin fragments in the tested sample. If the sample does not contain occludin fragments, only control line 22 will show color, as indicated in FIG. 3. A result where only test line 20 shows color or where there is no color at all indicates an invalid result and the test should be repeated with a new strip.

An alternate test strip embodiment is shown in FIGS. 6-10. The advantage of this system is that only a single occludin antibody is required. In this embodiment, as shown in FIG. 6, the strip 30 contains a sample pad 32, a conjugate pad 34, a membrane 36 and an adsorption pad 38. Colored colloidal-gold conjugated mouse IgG and colored colloidal-gold conjugated mouse anti-human antibody against human occludin are localized to conjugate pad 34. Membrane 36 defines a test region and includes a first control line 40, a test line 42, and a second test line 44. Goat anti-mouse IgG antibody is immobilized at control lines 40 and 44 while mouse anti-human antibody against human occludin is immobilized at test line 42. According to some embodiments, the concentration of goat anti-mouse IgG antibody immobilized to control lines 40 and 44 may differ substantially, for example by an order of magnitude, with the higher concentration being immobilized to line 44 and the lower concentration being immobilized to line 40. In use, a sample from the patient which is suspected to contain occludin fragments due to BBB disruption, such as a prepared or unprepared blood or spinal fluid sample is delivered to the sample pad. The fluid is then moved, via capillary action, to the conjugate pad, where the gold conjugated antibodies are dissolved in the fluid sample and moved to the test zone. As the fluid moves through the test region, the mouse IgG is first bound by the immobilized goat anti-mouse IgG antibody at control line 40, colorizing line 40. If occludin fragments are present in the sample, they will first bind the gold-conjugated antibody in conjugate pad 34, and then be immobilized to test line 42 via the bound antibody, thereby colorizing test line 42. Any remaining gold-conjugated mouse IgG that was not bound to control line 40, will then be bound at control line 44. Accordingly, a positive result is obtained if lines 40 and 42 are colored (FIG. 7) or if lines 40, 42, and 44 are colored (FIG. 8). A negative result is obtained if line 42 is not colored (FIGS. 9 and 10). An invalid result (not shown) is obtained if line 40 is not colored, whether or not lines 42 and 44 are colored. It is noted that, depending on the initial concentration of gold conjugated mouse IgG and concentration of goat anti mouse antibody immobilized at line 40, the presence or absence of color at line 44 is not necessarily indicated of a positive, negative, or invalid result. According to some embodiments, the concentration of immobilized antibodies at each of lines 40, 42, and 44, may be selected in order to make it possible to titer the occludin fragments, for example by comparing the intensity of line 42 with the intensities of lines 40 and 44, or by comparing the intensity of line 42 against a predetermined titer chart.

In both the examples shown in FIGS. 1-5 and 6-10 the various antibodies are described as being mouse or goat-derived antibodies. However, it will be understood that antibodies from other animals or natural or synthetic systems could be used so long as the appropriate and desired level of specificity is achieved. Furthermore, it will be understood that while the examples above are provided with reference to specific antibodies, similar tests could be designed using any of the OFBPs described above and that such tests including these OFBPs would then detect the presence and/or concentration of the particular fragments against which the OFBP has been designed or selected.

Figure 13:
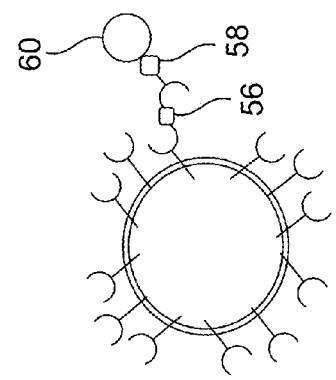
FIG. 13 is a schematic illustration of the bead of FIG. 11 having a complex formed from the mouse anti-human occludin antibody, an occludin fragment, a goat anti-mouse IgG Antibody with biotin tag, and Streptavidin-β-galactosidase attached thereto.
Figure 16:
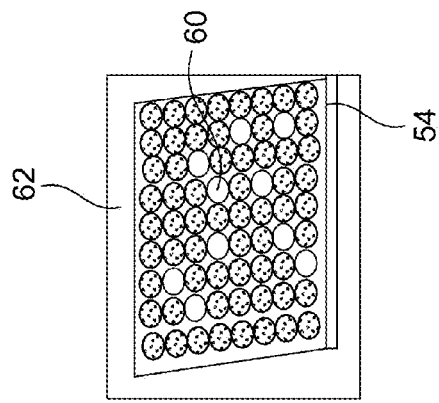
FIG. 16 shows another embodiment of the assay of FIGS. 11-13 after the detection step wherein the beads are magnetic and the wells are placed on a metal base.
Figure 12:
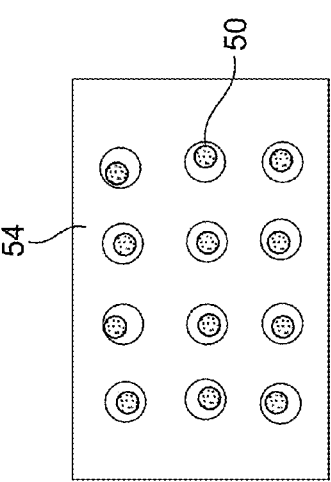
FIG. 12 is a schematic illustration of a plurality of wells the beads as shown in FIG. 11 disposed therein.
Figure 15:
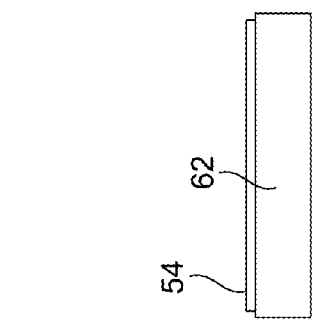
FIG. 15 shows another embodiment of the assay of FIGS. 11-13 wherein the beads are magnetic and the wells are placed on a metal base.
Figure 11:
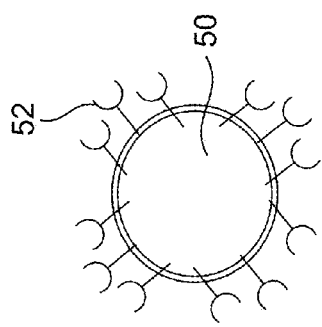
FIG. 11 is a schematic illustration of a bead to which mouse anti-human occludin antibodies are attached suitable for use in a bead-based assay system according to the present disclosure.
Figure 14:
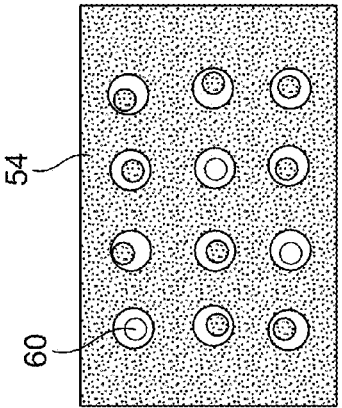
FIG. 14 is a schematic illustration of a fluorescence image after the bead-based assay of FIGS. 11-13 was performed.

An exemplary bead-based assay is shown in FIGS. 11-16. Turning first to FIG. 11, beads 50 are coated with a capture antibody such as mouse-anti human occludin antibody 52. Thousands of individual beads are then loaded into wells 54, as shown in FIGS. 12 and 15, and a fluid sample suspected of containing occludin fragments 56, a detection antibody 58, such as goat anti-mouse IgG antibody with a biotin tag and Streptavidin-B-galactosidase 60, as shown in FIG. 13, are introduced into the wells. As shown in FIG. 14, if occludin fragments are present in the sample, the occludin fragments will bind to the capture antibody and detection antibody, which, in turn, binds the streptavidin. Unbound reagents are then washed for the system. For example, as shown in FIGS. 15 and 16, the beads may be magnetic and the wells 54 placed on a metal base 62, so that the beads, and thus the captured antibody-complexes remain attached to the wells while non-bead-bound reagents are easily removed. The bound occludin fragments and accompanying fluorescent tags 60 can then be easily detected via fluorescence imaging, as depicted in the schematic representations shown in FIGS. 14 and 16.

According to yet another embodiment, some or all of the elements of the kit may be provided in the form of a microfluidic device which may include various compartments, channels, solutions, and components that enable the method to be practiced.

According to a still further embodiment, the presently described method may be practiced such that the detectable label indicates the concentration of occludin fragments in the blood sample. For example, the detection assay could be designed to produce results along a color or fluorescence intensity spectrum which correlates with the concentration of occludin fragments in the blood.

Accordingly, it will be appreciated that any components that are necessary for performing such any of the above-described detection-based assays could be included in a kit as described herein. Elements that may or may not be included in such a kit are not necessarily limited to, enzymes, ligands, fluorescent labels, dyes, solutions, vials, measuring instruments, and instructions.

According to various embodiments, any of the tests or kits described above could further include binding partners that are intended to act as an internal control. For example, as mentioned above and discussed in further detail below, our results indicate that claudin-5 and MMP-9 concentrations in the blood stream do not increase upon disruption of the blood brain barrier. According, test or kits of the present disclosure could further include binding partners for claudin-5 and/or MMP-9 to act as a comparison and internal control.

As stated above, the according to various embodiments the present disclosure provides for tests, kits, assays, or methods, that measure the presence and/or concentration of occludin fragments in a blood sample. According to some embodiments, the tests, kits, assays, or methods, may enable a care provider to determine whether a particular patient is eligible for tPA or other treatments, diagnoses, or actions based on the concentration of one or more types of occludin fragments present in a sample of the patient's blood. According to some embodiments, the occludin fragment may the fragment referred to herein as fragment 2 (or an amino acid sequence capable of binding an OFBP capable of binding fragment 2). According to some embodiments, the occludin fragment may the fragment referred to herein as fragment 1 (or an amino acid sequence capable of binding an OFBP capable of binding fragment 1).

According to some embodiments, the method, kit, test, assay, or the like, may indicate that a patient whose blood sample contains a concentration of fragment 2 (or an amino acid sequence capable of binding an OFBP capable of binding fragment 2) of greater than 1.5 µg/ml, greater than 1.75 µg/ml, or greater than 2 µg/ml is not eligible for tPA treatment and/or has suffered from an ischemic event and/or has substantial BBB damage. For the purposes of the present disclosure, the term "substantial BBB damage" is intended to mean that the damage is severe enough that red blood vessels are able to leak out of the blood vessels and administration of tPA is likely to cause intracebral hemorrhage, a major cause of stroke-induced death.

According to some embodiments, the method, kit, test, assay, or the like, indicate that a patient whose blood sample contains fragment 1 (or an amino acid sequence capable of binding an OFBP capable of binding fragment 1) has suffered from an ischemic event and/or has substantial BBB damage.

Figure 41:
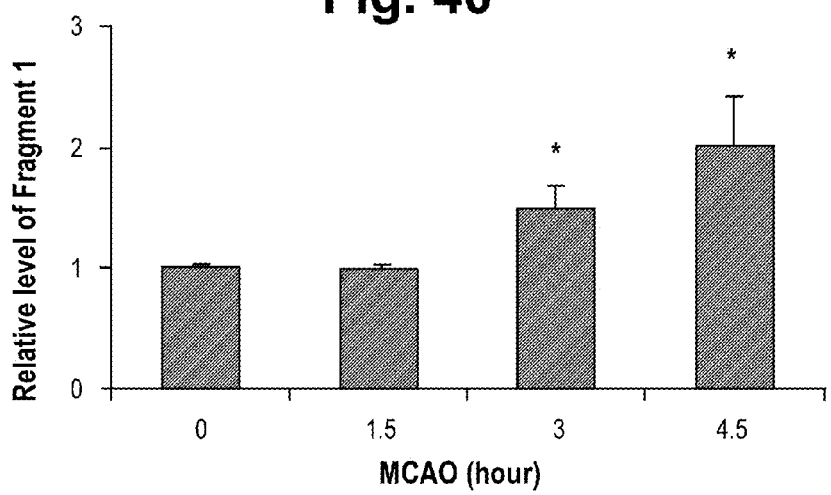
FIG. 41 is a graph showing quantified data from the ELISA assay.

According to some embodiments, the method, kit, test, assay, or the like may enable a care provider to periodically test blood samples over a period of time in order to determine whether the blood brain barrier has remained stable or is being damaged over time, for example as a result of injury, medication, or some other known or unknown cause. For example, as shown in FIG. 41 and described in greater below with respect to the Experimental section, we have seen that the concentration of Fragment 1 increases slowly and steadily over a 24 hour period. Accordingly, a test, kit, assay or the like that enables the quantification or relative concentration of fragment 1 in a patient's blood stream could be administered over periodic time points in order to monitor the progression of BBB damage, whether or not tPA is administered, and/or to determine when an ischemic event might have occurred (by, for example, extrapolating backwards based on occludin fragment 1 levels taken from the same patient at two or more time points.)

The present description makes frequent use of the term "blood sample." For the purposes of the present disclosure it will be understood that the blood sample may be prepared or unprepared prior to introduction to the assay system. For example, depending on the particular methodology being used a blood sample extracted from a patient may be spun to remove red blood cells and/or additional reagents may be added such as antibodies, antigens, and labels. Furthermore, it should be understood that other types of samples, such as spinal fluid may also include occludin fragments when the BBB is disrupted. Accordingly, it will be appreciated that all the above-described methods, assays, and kits are suitable for use with other types of fluids including spinal fluids, which may or may not be prepared prior to introduction into the assay system.

All patents and publications referenced below and/or mentioned herein are indicative of the levels of skill of those skilled in the art to which the invention pertains, and each such referenced patent or publication is hereby incorporated by reference to the same extent as if it had been incorporated by reference in its entirety individually or set forth herein in its entirety. Applicants reserve the right to physically incorporate into this specification any and all materials and information from any such cited patents or publications.

The specific methods and compositions described herein are representative of preferred embodiments and are exemplary and not intended as limitations on the scope of the invention. Other objects, aspects, and embodiments will occur to those skilled in the art upon consideration of this specification, and are encompassed within the spirit of the invention as defined by the scope of the claims. It will be readily apparent to one skilled in the art that varying substitutions and modifications may be made to the invention disclosed herein without departing from the scope and spirit of the invention. The invention illustratively described herein suitably may be practiced in the absence of any element or elements, or limitation or limitations, which is not specifically disclosed herein as essential. The methods and processes illustratively described herein suitably may be practiced in differing orders of steps, and that they are not necessarily restricted to the orders of steps indicated herein or in the claims. As used herein and in the appended claims, the singular forms "a," "an," and "the" include plural reference unless the context clearly dictates otherwise.

Under no circumstances may the patent be interpreted to be limited to the specific examples or embodiments or methods specifically disclosed herein. Under no circumstances may the patent be interpreted to be limited by any statement made by any Examiner or any other official or employee of the Patent and Trademark Office unless such statement is specifically and without qualification or reservation expressly adopted in a responsive writing by Applicants.

The terms and expressions that have been employed are used as terms of description and not of limitation, and there is no intent in the use of such terms and expressions to exclude any equivalent of the features shown and described or portions thereof, but it is recognized that various modifications are possible within the scope of the invention as claimed. Thus, it will be understood that although the present invention has been specifically disclosed by preferred embodiments and optional features, modification and variation of the concepts herein disclosed may be resorted to by those skilled in the art, and that such modifications and variations are considered to be within the scope of this invention as defined by the appended claims.

A greater understanding of the disclosed invention may be gained by review of the Examples below.

EXAMPLES

Cleavage of Occludin after Ischemic Onset

Blood brain barrier (BBB) disruption occurs early enough to be within the thrombolytic time window, and this early ischemic BBB damage is closely associated with hemorrhagic transformation and thus emerging as a promising target for reducing the hemorrhagic complications of thrombolytic stroke therapy. However, the mechanisms underlying early ischemic BBB damage remain poorly understood. Here we investigated the early molecular events of ischemic BBB damage using in vitro oxygen-glucose deprivation (OGD) and in vivo rat middle cerebral artery occlusion (MCAO) models. Exposure of bEND3 monolayer to OGD for 2 h significantly increased its permeability to FITC-labeled dextran, and promoted the secretion of metalloproteinase-2 and 9 (MMP-2/9) and cytosolic translocation of caveolin-1 (Cav-1). This same OGD treatment also led to rapid degradation of tight junction protein occludin and dissociation of claudin-5 from the cytoskeleton, which contributed to OGD-induced endothelial barrier disruption. Using selective MMP-2/9 inhibitor SB-3CT or their neutralizing antibodies or Cav-1 siRNA, we found that MMP-2 was the major enzyme mediating OGD-induced occludin degradation, while Cav-1 was responsible for claudin-5 redistribution. The interaction between Cav-1 and claudin-5 was further confirmed by co-immunoprecipitation. Consistent with these in vitro findings, we observed fluorescence tracer extravasation, increased gelatinolytic activity and elevated interstitial MMP-2 levels in ischemic subcortical tissue after 2-h MCAO. Moreover, occludin protein loss and claudin-5 redistribution were detected in ischemic cerebromicrovessels. These data indicate that cerebral ischemia initiates two rapid parallel processes, MMP-2-mediated occludin degradation and Cav-1-mediated claudin-5 redistribution, to cause BBB disruption at early stroke stages relevant to acute thrombolysis.

Materials and Methods

Cell culture. Mouse brain microvascular endothelial cells bEND3 (American Type Culture Collection) were grown as a monolayer in DMEM with 15% fetal bovine serum (FBS), 100 U/ml penicillin and 100 µg/ml streptomycin at 37° C. in a humidified incubators with 5% $CO_2$ and 95% room air. The cells were subcultured into 60 mm dishes coated with type I collagen (Nakamuta et al., 2005) and allowed to grow to confluence before exposure to OGD for 2 h. After OGD treatment, cell toxicity was measured by lactate dehydrogenase (LDH) assay using a CytoTox 96 Non-Radioactive Cytotoxicity Assay Kit (Promega). Besides endothelial cells, we also tested the effect of OGD on MMP-2/9 secretion in two mouse neural cell lines, C8-D1A (astrocyte) and SH-SY5Y (neuron). Both cell lines were purchased from American Type Culture Collection. C8-D1A cells and SH-SY5Y cells were cultured in DMEM or DMEM/F12 (1:1) (Sigma) containing 10% FBS, 100 U/ml penicillin and 100 µg/ml streptomycin, respectively. These cells were allowed to grow to 80-90% confluence before exposure to 2-h OGD treatment.

OGD treatment. To mimic acute ischemia-like conditions in vitro, bEND3 cells were exposed to OGD for 2 h as we described previously (Furuichi et al., 2005). In brief, confluent bEND3 cells were subjected to an ischemic injury by transferring cultures to glucose free medium (DMEM without glucose) pre-equilibrated with 95% N2 and 5% CO2. Cells were then incubated in a humidified airtight chamber (Billups-Rothberg Inc.) equipped with an air lock and flushed with 95% N2 and 5% CO2 for 15 min. The chamber was then sealed and kept at 37° C. for another 105 min. The oxygen concentration was below 0.2% as monitored by an oxygen analyzer (Sable Systems). Control cultures were incubated with normal DMEM medium without FBS for 2 h at 37° C. in 95% air and 5% CO2. Immediately after OGD treatment, the conditioned media (CM) and cells were collected separately for further analyses.

Preparation of total cell lysate, subcellular fractions. To reveal a redistribution of MMP-2/9, Caveolin-1 (Cav-1) and TJ proteins in OGD-treated bEnd3 cells, three subcellular fractions including membranous, cytosolic, and cytoskeletal fractions were extracted using ProteoExtract Subcellular Proteome Extraction Kit (Calbiochem) according to manufacturer's instruction. The specificity of each fraction was confirmed using anti-cytochrome Cypor (membrane/organelle fraction, MF), anti-calpain (cytosolic fraction, CF), and anti-vimentin (actin cytoskeletal fraction, ACF) antibodies. To extract total cell lysates, cells were lysed in RIPA buffer (Santa Cruz Biotech).

Endothelial cell monolayer permeability assay. The effect of OGD on endothelial monolayer permeability to fluorescein isothiocyanate conjugated 70-kDa dextran (FITC-dextran, Sigma) was assessed using Anopore membrane 24-well cell culture inserts with 0.2 µm pore size (Nunc). Cells were placed on the upper side of the insert and allowed to grow to confluence. FITC-dextran at a concentration of 3.5 µM (Eckle et al., 2008) was then added to the endothelial monolayer (luminal compartment) before exposing to 2-h OGD. After OGD treatment, the contents of FITC-dextran in both luminal and abluminal compartments were determined using a fluorescence plate reader Spectramax M2e (Molecular Devices Corp). Endothelial monolayer permeability was then assessed by calculating the apparent permeability coefficient (Papp) as previously described (Grabovac and Bernkop-Schnurch, 2006): Papp [cm/s]=dQ/(dt*A*Co), where dQ was the amount of FITC-dextran getting into the abluminal compartment, dt was duration of OGD treatment, dQ/dt was the rate of transfer (ng/s), A was surface area ($cm^2$), and Co was the initial concentration in the luminal chamber ($ng/cm^3$). To test whether MMP-2/9 and Cav-1 were implicated in OGD-induced endothelial barrier disruption, cells were treated with selective MMP-2/9 inhibitor SB-3CT (10 µM, Calbiochem) 2 h before and during OGD treatment or pretreated with Cav-1 siRNA for 48 h before OGD treatment.

SiRNA Transfection. bEnd3 cells at 60-70% confluence were transfected with 80 pmole of Cav-1 siRNA (Santa Cruz, sc-29520) or scrambled control siRNA (Santa Cruz Biotech, sc-37007) using siRNA Transfection Reagent (Santa Cruz Biotech) according to manufacturer's instruction. Forty-eight hours after transfection, cells were subjected to OGD treatment. Specific silencing was confirmed by western blot.

Gel gelatin zymography. After OGD treatment, MMP-2/9 in conditioned media (CM) and cellular extracts (CE) were analyzed by gelatin zymography as we described previously (Liu et al., 2007). In brief, equal amounts of CM or CE (containing 400 µg protein) were concentrated with gelatin-sephrose 4B beads (GE Healthcare). The MMP-2/9 were then eluted from gelatin beads by incubating with elution buffer (10% DMSO in PBS) and electrophoretically separated on 10% SDS-polyacrylamide gels co-polymerized with 1 mg/ml gelatin (Sigma) under nonreducing condition. Gels were washed in 2.5% Triton X-100 to remove SDS and then incubated for 48 h with a developing buffer containing 50 mM Tris, pH 7.6, 5 mM $CaCl_2$, 0.2 mM NaCl, and 0.02% (w/v) Brij-35 at 37° C. before staining with 0.125% Coomassie blue R-250. Gels were destained to visualize gelatinolytic bands (MMP-2/9) on a dark blue background. The intensities of MMP-2/9 bands were analyzed using the Kodak 4000 image station (Carestream Molecular Imaging). A mixture of human MMP-2/9 (Chemicon) was used as gelatinase standards.

MMP-2 and 9 antibody neutralization. To distinguish the role between MMP-2 and MMP-9 in mediating OGD-induced occludin degradation, we performed antibody neutralization experiments, as described previously (De Becker et al., 2007; Gong et al., 2008). In brief, 20 µg/ml of control mouse IgG (Santa Cruz Biotech.) or neutralizing antibodies (Millipore) against MMP-2, MMP-9 or both were added to confluent bEND3 cells right before 2-h OGD treatment. After OGD treatment, cells were lysed with RIPA buffer for assessing total occludin levels using western blot.

Communoprecipitation. Communoprecipitation was carried out as described previously (Wen et al., 2010). Briefly, bEND3 cells were subjected to OGD treatment for 2 h and then lysed on ice in 1 ml RIPA buffer. After pre-clearing with normal IgG, cell lysates (0.5 mg of protein) were incubated overnight at 4° C. with 2 µg of anti-Cav-1 (Santa Cruz Biotech.), followed by precipitation with 20 µl of protein A/G Plus-Agarose (Immunoprecipitation Reagent) for 1 h at 4° C. The precipitated complexes were separated on SDS-polyacrylamide gels and immunoblotted with anti-claudin-5 to detect the presence of this protein in the complex, as described below.

Western blot. Total cell lysates, subcellular fractions (CF, MF and ACF) (20 µg protein), and immunoprecipitates as prepared above were boiled and then electrophoresed in 12% SDS-PAGE acrylamide gels, transferred onto nitrocellulose membranes (Bio-Rad), and incubated for 1 h in TBS-T (Tris-buffered saline and 0.1% Tween 20) containing 5% nonfat milk. Membranes were then incubated overnight at 4° C. with primary antibodies against Cav-1 (Santa Cruz Biotech., 1:500), claudin-5 (Invitrogen, 1:1000) or occludin (Invitrogen, 1:500), washed in TBS-T, and incubated for 1 h at room temperature with corresponding HRP-conjugated anti-rabbit or anti-mouse antibodies (Santa Cruz Biotech., 1:1000). The membranes were developed with the SuperSignal West Pico HRP substrate kit (Pierce) and photographed on a Kodak 4000 image station (Carestream Molecular Imaging). To control sample loading and protein transfer, the membranes were stripped and reprobed with µ-actin antibody (Santa Cruz Biotech. 1:1000). For subcellular fraction samples, we noticed that the actin levels were comparable for each sample among different fractions, so we only used one normalizing loading control (CF actin) for all three subcellular fractions.

Real-time RT-PCR. Total cellular RNA was isolated using Trizol reagents (Invitrogen) according to manufacturer's protocol. 0.5 µg RNA was reverse-transcribed (RT) with random primers in a 20 µl final reaction volume using TaqMan® Reverse Transcription Kits (Applied Biosystems). 0.5 μl RT products were amplified with the 7900HT Fast Real-Time PCR System (Applied Biosystems) in a 10 μl final reaction volume using SYBR® Green PCR Master Mix (Applied Biosystems) under the following conditions: 2 min at 50° C. and 10 min at 95° C., followed by a total of 40 cycles of two temperature cycles (15 s at 95° C. and 1 min at 60° C.). Primers (Integrated DNA Technologies) for MMP-2, MMP-9 and glyceraldehydes 3-phosphate dehydrogenase (GAPDH) were designed against known mouse sequences: MMP-2 (NM_008610) forward: 5'-TAACCTG-GATGCCGTCGT-3' (SEQ ID NO:3), reverse: 5'-TTCAG-GTAATAAGCACCCTTG-3' (SEQ ID NO:4); MMP-9 (NM_013599) forward: 5'-ACGACATAGAC GGCATCCA-3' (SEQ ID NO:5), reverse: 5'-GCTGTGGT-TCAGTTGTGGTG-3' (SEQ ID NO:6); GAPDH (NM_008084) forward: 5'-CAATGTGTCCGTCGT GGATCT-3' (SEQ ID NO:7), reverse: 5'-GTCCTCAGTG-TAGCCCA AGATG-3' (SEQ ID NO:8). The fluorescence threshold value (Ct value) was calculated using the SDS Enterprise Database software (Applied Biosystems). The relative value of mRNA expression was calculated by the comparative μDCt method described in our previous publication (Liu et al., 2007). In brief, mean Ct values were normalized to the internal control GAPDH and the difference was defined as ΔCt. The difference between the mean ΔCt values of treated and untreated cells was calculated and defined as ΔΔCt. The comparative mRNA expression level was expressed as $2^{-\Delta\Delta Ct}$.

Immunostaining of occludin and claudin-5 in OGD-treated bEND3 cells. The bEND3 cells grown to confluence on collagen-coated coverslips were subjected to the indicated treatments. For immunostaining, cells were washed 3 times with PBS, fixed in 4% paraformaldehyde for 10 min, permeabilized with 0.1% Triton X-100 for 5 min, and then blocked for 1 h at room temperature with 3% BSA+0.1% Tween-20+5% goat serum. The cells were then incubated with anti-occludin or anti-claudin-5 primary antibodies (1:100 dilution, Invitrogen) overnight at 4° C., followed by incubation with FITC or Cy3 conjugated anti-mouse or anti-rabbit second antibodies (1:200 dilution) for 60 min. After washing in PBS, the coverslips were mounted on glass slides with anti-fade solution Vectashield (Vector Laboratories). Images were acquired using an LSM 510 confocal laser-scanning microscope (Zeiss).

Rat model of middle cerebral artery occlusion (MCAO). The Laboratory Animal Care and Use Committee of the University of New Mexico approved all experimental protocols. Male Sprague Dawley rats (Charles River Laboratories, Wilmington, Mass., USA) weighing 290 to 320 g were anesthetized with isoflurane (4% for induction, 1.75% for maintenance) in N20:02 (70%:30%) during surgical procedures and the body temperature was maintained at 37.5° C.±0.5° C. using a heating pad. The rats were subjected to 2 h of reversible MCAO using the intraluminal filament technique as previously described (Liu et al., 2009b). Briefly, a 4-0 silicone-coated monofilament nylon suture was inserted into the internal carotid artery and advanced along the internal carotid artery to approximately 17 to 18 mm from the bifurcation, thereby blocking the ostium of the MCA. Because we aimed to investigate ischemia-induced early changes in MMP-2/9 and BBB permeability, rats were not reperfused when collecting microdialysis samples for MMP-2/9 measurement or reperfused for only 10 min when assessing BBB damage (as described below). For a total number of 38 rats included in this study, successful MCAO was confirmed by 2,3,5-triphenyltetrazolium chloride (TTC) staining of the 1-mm thick brain coronal section 6 mm away from the tip of the front lobe as we described previously (Liu et al., 2008).

Evaluation of ischemia-induced BBB damage. To visualize ischemia-induced BBB damage, all rats received femoral vein injections of 30 mg/kg body weight FITC-albumin (25 mg/ml in sterile PBS) at the end of 2 h-MCAO. Then the rats were reperfused for 10 min to ensure sufficient circulation of fluorescent tracer to the ischemic brain and also minimize the effect of reperfusion on BBB permeability. At the end of reperfusion, rats were transcardially perfused with 250 ml cold PBS to remove intravascular FITC-albumin. The brain was then removed and a 5-mm-thick brain region 7 mm away from the tip of the front lobe was rapidly frozen in methylbutanol pre-chilled in a −80° C. freezer. Twenty-μm-thick cryosections were cut with a Leica cryostat (Leica Microsystems) and mounted for fluorescence microscopic observation at an excitation wavelength of 485 nm and a 528-nm filter for collecting fluorescence emission (Olympus IX-81, Olympus). The whole brain coronal section was automatically photographed (10×Objective lens) using the Stero Investigator software to visualize FITC-albumin leakage (BBB disruption), which appeared as green fluorescence on brain sections.

Evaluation of MMP-2/9, occludin and claudin-5 changes in ischemic tissue with BBB damage. In situ zymography and immunohistochemistry (IHC) were performed to analyze the gelatinolytic activities of MMP-2/9 and occludin/claudin-5 protein levels in ischemic tissue with compromised BBB, respectively. In these experiments, FITC-albumin was replaced with Texas red-conjugated albumin (Texas red-albumin, Sigma) to label ischemic tissue with BBB damage because FITC-albumin may interfere with in situ zymography analysis in which FITC-labeled DQ-gelatin is used as a substrate. At the end of 2-h MCAO and 10-min reperfusion, rats were transcardially perfused, and the same 5-mm-thick brain region was cut out and frozen in pre-chilled 2-methylbutane, as described above. Ten-μm-thick and 20-μm-thick cryosections were prepared for IHC or in situ zymography analysis, respectively, as described below.

The 10-μm-thick cryosections were fixed with 4% PFA for IHC analysis for occludin and claudin-5 as we described previously (Yang et al., 2007b; Liu et al., 2009b). In brief, non-specific binding sites were blocked by pre-incubating tissue for 1 h at room temperature in PBS containing 0.1% Triton X-100, 1% BSA, and 5% goat serum. Sections were then incubated overnight with Alexa Fluor 488-conjugated claudin-5 antibody (1:100 dilution, Invitrogen) or anti-FITC-conjugated occludin antibody (1:100 dilution, Invitrogen) at 4° C. Immunostaining was visualized under LSM 510 confocal laser-scanning microscope (Zeiss), and images were taken from the ischemic region with Texas red-albumin leakage and the mirrored regions on the nonischemic hemisphere.

The 20-μm-thick cryosections were used for analyzing gelatinolytic activities of MMP-2/9 by in situ zymography as we described previously (Liu et al., 2009b). In brief, the section was incubated for 2 h at 37° C. in a reaction buffer containing 40 μg/ml of FITC-labeled DQ-gelatin (Invitrogen). FITC-gelatin is cleaved by gelatinases, yielding peptides whose fluorescence is representative of the net gelatinolytic activity. At the end of incubation, sections were rinsed with PBS and mounted in Gel/Mount (Biomeda) for fluorescence microscopy (Olympus). Images were taken from the ischemic region with Texas red-albumin extravasation and the mirrored region on the nonischemic hemisphere.

Isolation of cerebral microvessels. Isolation of cerebral microvessels was performed as we described previously (Liu et al., 2009b). In brief, the hemispheric brain tissue was dissected and homogenized in ice-cold PBS. The homogenate was filtered through a 41-μm nylon mesh (Spectrum), and the nylon mesh was washed three times with PBS. Microvessels retained on the mesh were then washed off and pelleted by centrifugation at 4000 g for 10 min at 4° C. The pellets were resuspended in 15% dextran T-500 and then added onto 20% dextran T-500, followed by centrifugation at 25,000 g for 10 min at 4° C. The pellets were collected as the cerebral microvessels and stored at −80° C. until further analysis. To determine the redistribution of claudin-5, we pooled the hemispheric microvessels isolated from 3 rats to get enough protein for preparing the subcellular fractions with ProteoExtract Subcellular Proteome Extraction Kit (Calbiochem).

In vivo microdialysis sampling. Microdialysis sampling is a well-established diffusion-based sample collection method for collecting molecules including MMPs from the interstitial space in a specific tissue or organ in situ (Liu et al., 2003; Nilsson and Dabrosin, 2006; Wang et al., 2009). The conventional MMP extracting method (tissue homogenization) is not able to separate intracellular MMPs from extracellular MMPs produced in the ischemic brain, therefore we applied the in vivo microdialysis sampling to collect MMPs in the interstitial space of the ischemic brain tissue. Prior to conducting MCAO surgery, two microdialysis guide cannulas were surgically placed separately into left and right striatum using the coordinates of 0.3 mm posterior to bregma, 4 mm lateral to the midline and 7 mm below the surface of the brain according to a previous study in our lab (Liu et al., 2003). Then the guide cannulas were removed and rats were subjected to MACO surgery. Right after ischemia onset, rats were placed back to the stereotactic device for microdialysis probe implantation. Under isoflurane anesthesia, two identical PES probes (CMA 12, 4 mm, 100 kDa cut-off membrane) (CMA Microdialysis) which were pre-perfused with 70% ethanol then sterile water were inserted into the left and right striatum along the guide cannulas. Then, the inlet and outlet tubing were connected to a CMA 102 microdialysis dual-channel pump (CMA Microdialysis). Rats were under anesthesia during sample collection. Both probes were perfused with sterile artificial cerebrospinal fluid with the following sequence 5 μl/min for 10 min, 2 μl/min for 10 min (these perfusates were discarded), and then 2 μl/min for around 90 min until the end of 2 h-MCAO. The perfusate collected in the last 90 min of perfusion was used for measuring MMP-2/9 with zymography. The 5 μl/min flush for the first 10 min was performed ensure that fluid lines were open after the implantation of the probe. Additionally, as microdialysis sampling is an invasive procedure, any solutes released due to the surgery or probe insertion into the tissue will be flushed out with a higher flux as mass removal during microdialysis sampling is directly correlated with perfusion flow rate. After completion of the dialysate collection, rats were sacrificed and the brains were removed and sectioned at 1 mm intervals. The probe placement was confirmed by visual observation.

In addition, to determine whether MMP-2/9 induction contributed to MMP-2/9 changes in the interstitial space of the ischemic striatum, we performed another set of experiments to assess MMP-2/9 mRNA expression in the striatal tissue after 2-h MCAO. Striatal tissue was dissected, and total RNA was isolated using Trizol reagents and subjected to real-time RT-PCR analysis as described above. Primers for rat MMP-2, MMP-9 and house-keeping gene rpl 32 were the same as described in our previous study (Liu et al., 2007). MMP-2 (U65656) forward: 5'-GATCTG-CAAGCAAGACATTGTCTT-3' (SEQ ID NO:9), reverse: 5'-GCCAAATAA ACCGATCCTTGAA-3' (SEQ ID NO:10); MMP-9 (U24441) forward: 5'-GTAACCCTGGT-CAC CGGACTT-3' (SEQ ID No:11); reverse, 5'-ATACGT-TCCCGGCTGATCAG-3' (SEQ ID NO:12); rpl 32 (NM_013226) forward: 5'-AGACCTGAATGT-GAAGGAAG-3' (SEQ ID NO: 13), reverse: 5'-CCT-TGGGATTGGTGACTCTGA-3' (SEQ ID NO: 14).

Statistical analysis. All data were presented as means±SE. Differences between groups were assessed by Student's t test or ANOVA followed by Tukey's post hoc test as indicated in the Figure Legends. A value of $p \leq 0.05$ was considered statistically significant.

Results

Ischemia Rapidly Disrupts the Endothelial Barrier in vitro and in vivo

Figure 17A:
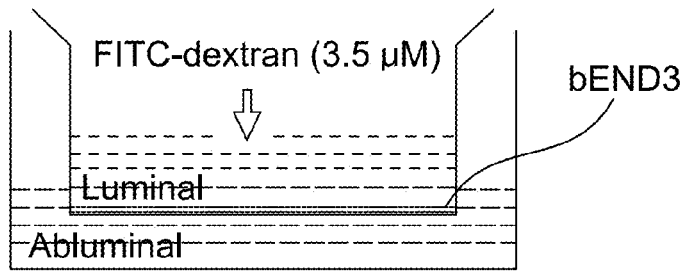
FIG. 17a is a schematic representation of the in vitro BBB model (bEND3 monolayer grown on an insert) with FITC-dextran loaded in the luminal compartment.
Figure 17B:
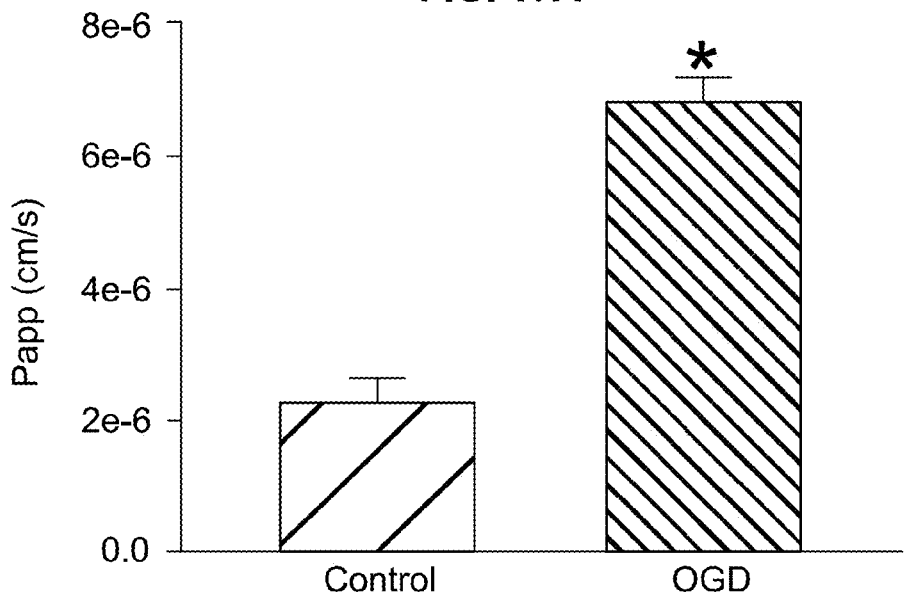
FIG. 17b is a graph showing the assessment of endothelial monolayer permeability by calculating the transfer rate of FITC-dextran from luminal compartment to the abluminal compartment and expressed as an apparent permeability coefficient (Papp) (in centimeters per second). Exposure of bEND3 monolayer to OGD for 2 h significantly increased its permeability to FITC-dextran. *p<0.05 versus control cultures, Student's t test; n=6.
Figure 18:
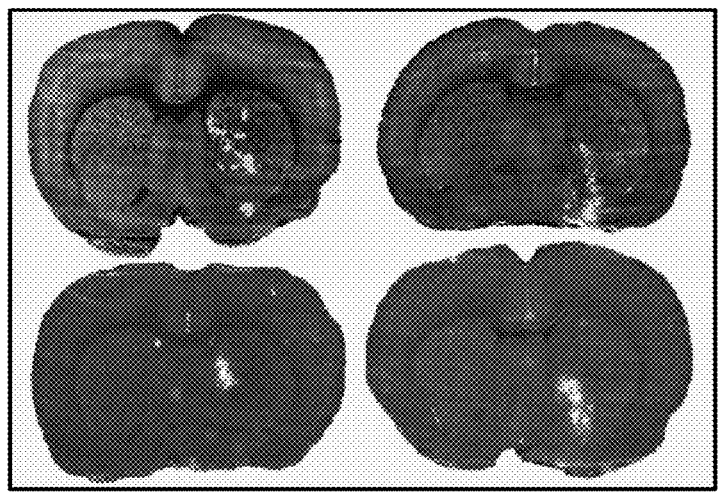
FIG. 18 is representative fluorescence micrographs of brain cryosections from four different rats revealing 2 h MCAO induced FITCalbumin extravasation (bright green fluorescence) in the subcortical regions in the ischemic hemisphere. No FITC-albumin leakage was observed in other brain regions. Cerebral ischemia rapidly induced BBB disruption in the ischemic brain of all tested rats (n=6).

In view of the close association between ischemia-induced initial BBB damage and the hemorrhagic complications of acute stroke thrombolysis (Hjort et al., 2008; Kastrup et al., 2008; Kassner et al., 2009; Sun et al., 2010), we sought to understand how cerebral ischemia affects BBB integrity within the established 3-h thrombolytic time window in vitro and in vivo. Brain endothelial monolayers challenged with OGD are frequently used as an in vitro model of ischemic BBB damage (Benchenane et al., 2005; Zhu et al., 2010). We exposed confluent brain microvascular endothelial cells (bEND3) grown on 24-well cell culture inserts to 2 h-OGD without re-oxygenation. The barrier integrity of the endothelial monolayer in control condition or after 2 h-OGD treatment was assessed by measuring the transfer rate (Papp) of FITC-dextran from the luminal compartment to the abluminal compartment (FIG. 17). OGD treatment significantly sped up the passage of FITC-dextran across the endothelial monolayer, indicating disruption of its barrier function (FIG. 18). To determine whether cytotoxicity contributed to OGD-induced permeability increase of the endothelial monolayer, we also evaluated cytotoxicity with a lactate dehydrogenase (LDH) assay kit, and found that OGD under our experimental conditions did not increase LDH release into the cell culture supernatant (data not shown), indicating that OGD-induced endothelial monolayer barrier dysfunction was not due to a direct toxic effect on endothelial cells.

We also examined the effect of cerebral ischemia on BBB integrity on an in vivo rat model of 2-h MCAO. Since post-ischemic reperfusion can exacerbate BBB damage (Simard et al., 2007), we reperfused the MCAO rats for a brief 10-min duration to allow sufficient circulation of FITC-albumin to the ischemic brain region, while minimizing the impact of reperfusion on the BBB. As seen on the fluorescent micrographs of representative brain cryosections (FIG. 18), 2-h MCAO consistently induced FITC-albumin extravasation in the ischemic hemisphere, and the leakages were invariably seen in the subcortical regions. These in vitro and in vivo data clearly indicate that ischemia causes BBB disruption at an early stroke stage (within 2 h after ischemia onset) relevant to acute stroke thrombolysis.

OGD Triggers Occludin Loss and Claudin-5 Redistribution in Endothelial Cells

Figure 19:
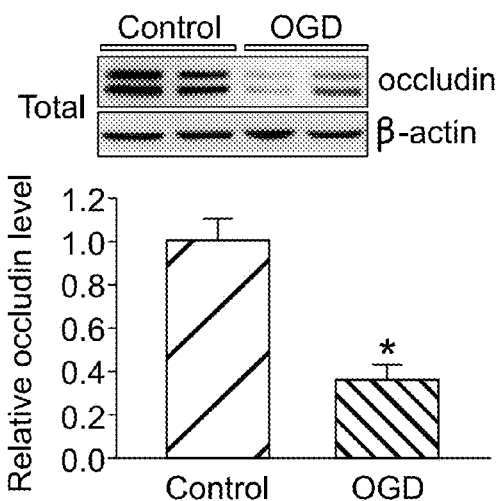
FIG. 19 shows the results of Western blot analysis for the tight junction protein occludin. Two hour OGD induced a significant reduction in total occludin protein level.
Figure 20:
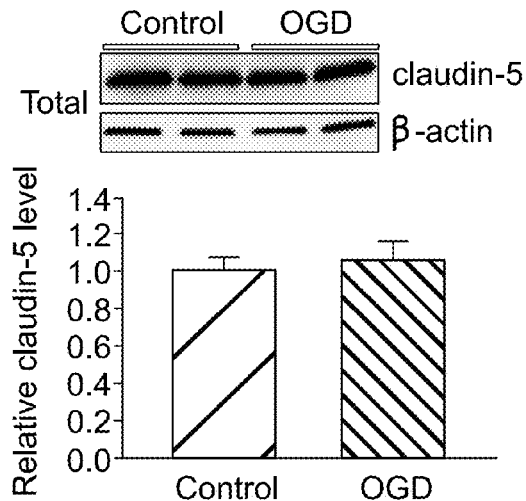
FIG. 20 shows the results of Western blot analysis for the tight junction protein claudin-5. Two hour OGD did not induce a significant reduction in total claudin-5 protein level.
Figure 21:
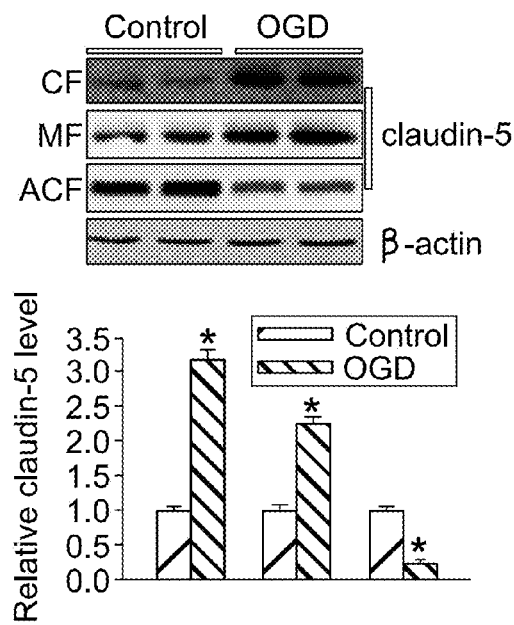
FIG. 21 shows the results of Western blot analysis after OGD induced redistribution of claudin-5 between subcellular compartments, as reflected by a remarkable reduction in claudin-5 levels in the ACF and a significant increase of its levels in the CF and MF. The blots for CF were stripped and reprobed with β-actin antibody.
Figure 22:
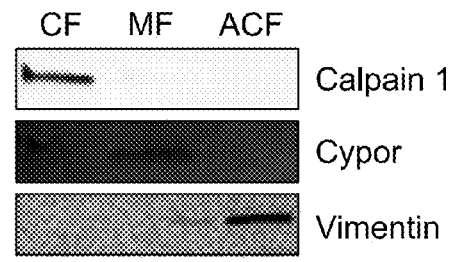
FIG. 22 shows confirmation of the specificity of each fraction with anti-calpain (CF), anti-Cypor (MF), and anti-vimentin (ACF) antibodies. *p<0.05 versus control, Student's t test; n=4. Error bars indicate SEM.

Altered distribution of TJ proteins, particularly claudins and occludin, or their loss are frequently seen in the compromised BBB following cerebral ischemia and reperfusion (Yang et al., 2007b; McColl et al., 2008; Liu et al., 2009b). To determine whether the rapid disruption of endothelial barrier function observed above was due to a quick disturbance on TJ proteins by ischemia, we investigated the effect of 2-h OGD on two important transmembrane TJ proteins claudin-5 and occludin (FIG. 19-22). Total cellular extracts of control bEND3 cells exhibited readily detectable protein bands of occludin and claudin-5 on the immunoblots. Occludin exhibited as a doublet of 60 and 65 kDa on western blot, which represents two different isoforms of occludin monomers (McCaffrey et al., 2007). Following 2-h OGD insult, bEND3 cells manifested a dramatic reduction in the total protein level of occludin (FIG. 19). Surprisingly, OGD treatment did not change the total protein levels of claudin-5 (FIG. 20). Besides total protein levels, redistribution of TJ proteins, particularly their dissociation from the cytoskeletal framework, also contributes to BBB compromise (Song and Pachter, 2004; Song et al., 2007). To monitor the redistribution of occludin and claudin-5 in OGD-treated cells, we prepared subcellular fractions to detect the translocation of occludin and claudin-5 between subcellular compartments. As shown in FIG. 21, OGD treatment led to a significant increase in claudin-5 levels in the detergent soluble fractions including the cytosolic fraction (CF) and membrane/organelle fraction (MF) and a concurrent decrease in its level in the detergent resistant actin cytoskeleton fraction (ACF), indicating a dissociation of claudin-5 from the cytoskeletal framework under OGD condition. Unlike claudin-5, occludin was uniformly decreased in all tested subcellular fractions, but did not exhibit any redistribution changes after OGD insult (Data not shown). The characterization of the subcellular fractions was verified by the presence of specific marker protein in each fraction (FIG. 22). These data suggest that OGD triggers rapid loss of occludin protein and rapid dissociation of claudin-5 from the cytoskeleton framework.

Figure 23:
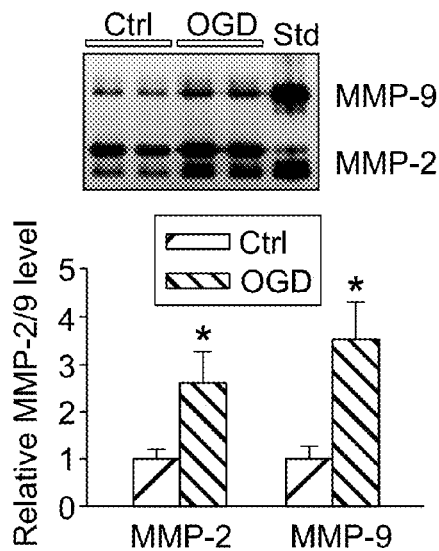
FIG. 23 is the results of a Western blot showing that OGD rapidly elevated MMP-2/9 levels in conditioned media. After exposure of bEND3 cells to OGD for 2 h, a significant increase in MMP-2/9 levels was detected in the conditioned medium on gelatin zymograms when compared with the control cultures (Ctrl). Active MMP-2 (the bottom band), but no active MMP-9, was seen on zymogram gels. MMP-2 or -9 levels were quantified by measuring the sum intensity of their latent and active bands. *p 0.05 versus Ctrl, Student's t test; n=5. Std, Standard human MMP-2/9.

MMP-2/9 Contribute to Occludin Loss, but not Claudin-5 Redistribution in OGD-treated Endothelial Cells We next examined the mechanisms underlying the rapid changes of TJ proteins under OGD condition. MMP-2/9 have been shown to proteolytically disrupt TJ proteins under various pathological conditions including ischemic stroke (Yang et al., 2007b; McColl et al., 2008; Liu et al., 2009b; Lischper et al., 2010). Therefore, we asked if MMP-2/9 were involved in OGD-induced disturbance in TJ proteins. To test this possibility, we first examined whether OGD could affect MMP-2/9 levels in bEND3 cells in an ischemic duration as short as 2 h. Since MMP-2/9 are synthesized intracellularly and secreted into the extracellular space to digest matrix components (Taraboletti et al., 2006), we assessed MMP-2/9 levels in the CM using gel gelatin zymography, the most widely used method for detecting MMP-2/9, which reveals proteolytic bands on zymogram gels derived from both pro- and active forms of MMP-2/9 (Min et al., 2006). Under control conditions, latent MMP-9 and both latent (upper band) and active (lower band) forms of MMP-2 were detected in the CM of bEND3 cells, according to standard MMP-2/9 bands (FIG. 23). Following 2-h OGD treatment, MMP-2/9 levels were significantly increased in the CM, while their activation patterns did not change (FIG. 23). For this reason, we did not separately label the latent and active MMPs on the zymogram gels, but rather called them together as MMP-2 or MMP-9.

Figure 24:
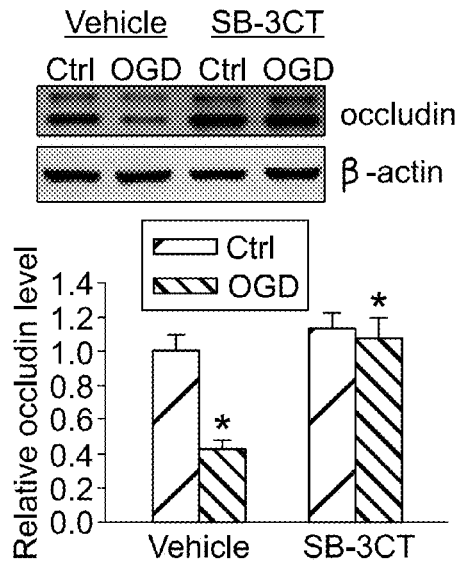
FIG. 24 is the results of a Western blot showing selective MMP-2/9 inhibitor SB-3CT completely inhibited OGD-induced occludin degradation. bEND3 cells were treated with SB-3CT (10 μM) 2 h before and during 2 h OGD. Occludin protein in total cellular extracts was detected with Western blot. β-Actin served as a loading control. *p<0.05 versus vehicle (DMSO) plus Ctrl, #p<0.05 versus vehicle plus OGD, ANOVA; n=5.
Figure 25:
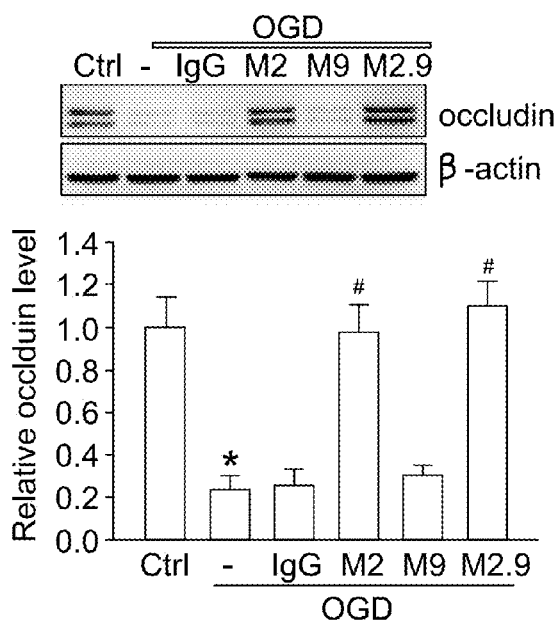
FIG. 25 is the results of a Western blot showing MMP-2 neutralizing antibody (M2) completely inhibited OGD-induced occludin degradation, while no significant effects were observed for IgG or MMP-9 neutralizing antibody (M9). bEND3 cells were treated with 20 μg/ml control mouse IgG, MMP-2 or MMP-9 neutralizing antibodies, or both (M2,9) during 2 h OGD. Occludin protein in total cellular extracts was detected with Western blot. β-Actin served as a loading control. *p<0.05 versus control (Ctrl), #p<0.05 versus OGD alone (−) or OGD plus IgG, ANOVA; n=4.

Next, we investigated whether OGD-induced alteration in occludin and claudin-5 was dependent on the proteolytic activity of MMP-2/9. Using the highly selective, mechanism-based potent MMP-2/9 inhibitor SB-3CT (Brown et al., 2000), we found that inhibition of MMP-2/9 completely abolished OGD-induced occludin reduction in bEND3 cells (FIG. 24). Worthy of note, SB-3CT-treated control bEND3 cells also exhibited a slight increase (not statistically significant) in occludin level compared to vehicle-treated cells (DMSO, final concentration of 1/1000 in volume ratio), suggesting that MMP-2/9 may play a role in maintaining the normal turnover of occludin under control conditions. To further distinguish between the roles of MMP-2 and MMP-9 in mediating OGD-induced occludin degradation, we selectively immunodepleted MMP-2, MMP-9, or both using neutralizing antibodies. The blocking of MMP-2, but not MMP-9, by neutralizing antibody significantly inhibited OGD-induced occludin degradation compared with control IgG (FIG. 25). To test effectiveness of MMP-9 neutralizing antibody, we incubated bEND3 extracts with active MMP-9 (5 µg/ml, R&D system) in the presence or absence of 20 µg/ml MMP-9 neutralizing antibody, and found that the presence of MMP-9 antibody significantly inhibited active MMP-9-induced occludin degradation (data not shown). These results indicate that MMP-2 is the major gelatinase contributing to occludin degradation after 2-h OGD, which is in agreement with our observation that the active form of MMP-2, but not active MMP-9, was detected in OGD-treated bEND3 cells (FIG. 23).

Figure 26:
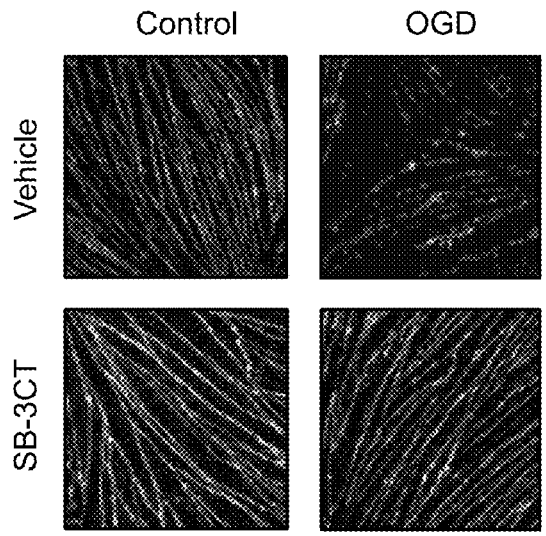
FIG. 26 presents representative confocal micrographs showed MMP-dependent degradation of occludin. Control bEND3 cells revealed a circumcellular immunostaining of occludin, which was significantly reduced after exposing cells to OGD for 2 h. SB-3CT treatment completely inhibited occludin reduction in OGD-treated cells. Experiments were repeated three times with similar results. Scale bar, 20 μm.
Figure 27:
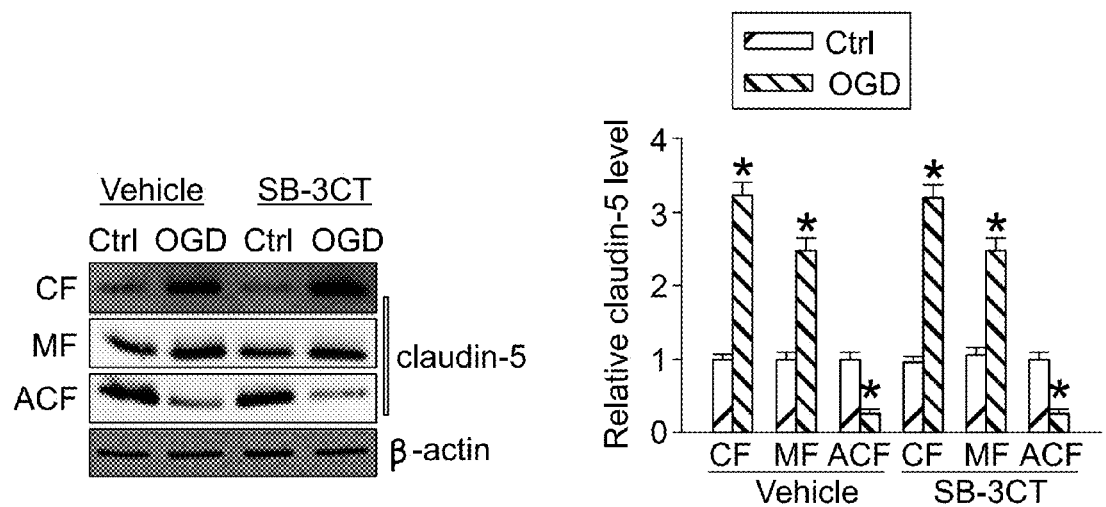
FIG. 27 is the results of a Western blot showing Inhibition of MMP-2/9 with SB-3CT had no effect on OGD-induced claudin-5 redistribution. Claudin-5 proteins in subcellular fractions were detected with Western blot. *p<0.05 versus vehicle plus Ctrl, ANOVA; n=5. Error bars indicate SEM.

To further confirm a gelatinase-dependent degradation of occludin under OGD conditions, we performed immunofluorescence staining to visualize the changes of occludin in OGD-treated cells in the presence of SB-3CT. Confocal microscopic images revealed a circumcellular staining for occludin protein in control bEND3 cells, regardless of whether they were treated with vehicle or SB-3CT (FIG. 26, left panels). Consistent with the western blot results, exposure of cells to OGD for 2 h significantly reduced the immunostaining of occludin, and this reduction was completely inhibited when cells were pretreated with SB-3CT (FIG. 26, right panels). It is worthy of note that SB-3CT-treated control cells appeared to exhibit a slight stronger immunostaining (brighter fluorescence) for occludin than vehicle-treated control cells (FIG. 26, left panels). In contrast to occludin, OGD-induced changes in claudin-5 were not dependent on MMP-2/9 because SB-3CT had no effect on its redistribution between subcellular fractions (FIG. 27). In summary, these data indicate that OGD rapidly elevates extracellular MMP-2/9 levels, and that the active MMP-2 is the key effector molecule responsible for the rapid loss of occludin protein, but not for claudin-5 protein redistribution, in endothelial cells under ischemic condition.

Figure 28:
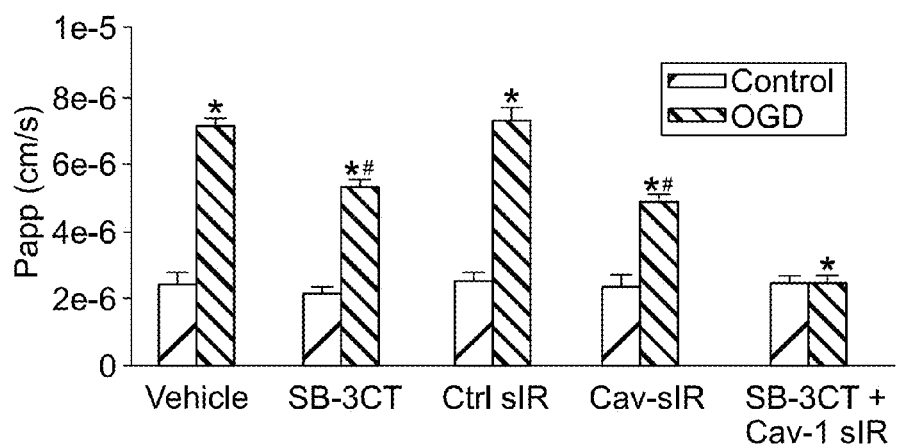
FIG. 28 is a graph showing Inhibition of MMP-2/9 with SB-3CT or knockdown of Cav-1 with siRNA reduces OGD-induced BBB disruption in vitro. The permeability of FITC-dextran across bEND3 monolayers was significantly increased after 2 h exposure to OGD, which was partially inhibited by pretreating cells with MMP-2/9 inhibitor SB3-CT or Cav-1 siRNA. Combination of SB-3CT and Cav-1 siRNA completely preserved the endothelial barrier integrity of OGD-treated endothelial monolayer. The endothelial monolayer permeability was assessed by calculating the transfer rate of FITC-dextran from luminal compartment to abluminal compartment, and was expressed as apparent permeability coefficient (Papp) (in centimeters per second). *$p<0.05$ versus control; #$p<0.05$ versus vehicle-OGD cultures; $^{\Phi}p<0.05$ versus control siRNA (Ctrl siR) plus OGD; $^{\&}p<0.05$ versus Cav-1 siRNA (Cav-1 siR) plus OGD or SB-3CT plus OGD, ANOVA; n=6. Error bars indicate SEM.

Knockdown of Cav-1 or Inhibiting MMP-2/9 Reduces OGD-induced Disruption of the Endothelial Barrier In view of the critical role of claudin-5 and occludin in maintaining normal endothelial barrier function, we next examined whether MMP-mediated occludin degradation and Cav-1-dependent redistribution of claudin-5 were responsible for OGD-induced endothelial barrier disruption (FIG. 17). We pre-treated bEND3 cells with specific MMP-2/9 inhibitor SB-3CT or Cav-1 siRNA before exposing the cells to 2-h OGD. As expected, scrambled control siRNA or Vehicle (DMSO, final concentration of 1/1000 in volume ratio) did not affect endothelial monolayer permeability to FITC-dextran for both control cultures and OGD-treated cells when compared with the results in FIG. 17. Notably, SB-3CT or Cav-1 siRNA alone significantly reduced the permeability of OGD-treated endothelial monolayer to FITC-dextran, and their combination treatment completely prevented endothelial barrier compromise (FIG. 28). These results indicate that OGD-induced early changes in tight junction proteins occludin and claudin-5 are responsible for rapid loss of endothelial barrier function under ischemic condition.

2-h MCAO Induces MMP-2/9 Increase in Tissue Interstitial Space, Occludin Loss and Claudin-5 Redistribution in Ischemic Cerebromicrovessels To validate our findings in vitro, we next examined the effects of 2-h MCAO on MMP-2/9, TJ protein occludin and claudin-5 in ischemic brain tissue. First, we performed in situ zymography on cryosections obtained from brain tissue injected with Texas red-albumin to examine the gelatinolytic activity of MMP-2/9. As shown in FIG. 29, increased gelatinolytic activity (bright green fluorescence) was only observed in ischemic striatal tissue that showed concurrent extravasation of Texas red-albumin. No tracer leakage and weak gelatinolytic activity were observed in non-ischemic striatal tissue. To demonstrate a MMP-secreting mechanism in vivo, we assessed extracellular MMP-2/9 levels in the ischemic brain tissue using in vivo microdialysis sampling. We inserted the microdialysis probes into the striatal tissue because the striatum was referred to as an "ischemic core" region that exhibited very low residual cerebral blood flow after MCAO (Butcher et al., 1990) and higher susceptibility of its microvasculature to ischemic injury (Nagaraja et al., 2011), and our results showed BBB disruption in this region after 2-h MCAO (FIG. 18). FIG. 30 showed the schematic diagram for microdialysis sampling. Gel gelatin zymography analysis showed that 2-h MCAO induced a significant increase in MMP-2 in the interstitial space of the ischemic striatal tissue compared to its nonischemic counterpart. MMP-2 seemed to be the major form of the secreted gelatinases in the ischemic striatum because MMP-9 was barely seen on the zymogram gels (FIG. 31). To determine whether 2-h MCAO upregulated MMP-2/9 expression, we extracted total RNA from the striatal tissue and analyzed MMP-2/9 mRNA expression. As shown in FIG. 32, 2-h MCAO did not change MMP-2/9 mRNA expression in the ischemic striatum. These in vivo data suggest that cerebral ischemia leads to a rapid accumulation of extracellular MMP-2 in the ischemic brain through promoting their secretion, rather than stimulating their synthesis in an early stroke stage relevant to acute stroke thrombolysis.

Next, IHC and immunoblotting were conducted to detect the changes of TJ protein claudin-5 and occludin in the ischemic brain after 2-h MCAO. We performed IHC on cryosections obtained from brain tissue injected with Texas red-albumin and found that the immunostaining of occludin (FIG. 33), but not claudin-5, was significantly reduced in ischemic striatal tissue that showed Texas red-albumin extravasation, when compared to nonischemic striatal tissue. However, we did not see subcellular redistribution of claudin-5 even under higher magnification (63× objective, data not shown), which was observed in OGD-treated bEND3 cells. To confirm these IHC results, we performed western blot to detect the changes of occludin and claudin-5 in cerebral microvessels isolated from ischemic brain tissue. In consistent with the IHC results, 2-h MCAO induced a significant reduction in occludin protein levels (FIG. 35), while did not change the total levels of claudin-5 protein (FIG. 36, left upper panel). Notably, through measuring claudin-5 contents in subcellular fractions of microvascular extracts, we found that 2-h MCAO induced increases in claudin-5 in the CF and MF, while decreased its contents in the ACF (FIG. 36, right upper and bottom panels). These results indicate that cerebral ischemia leads to rapid occludin degradation and claudin-5 redistribution in vivo.

CONCLUSION

The above-described experiments found that 2-h OGD induced a significant reduction in the TJ protein occludin. These results also indicate that MMP-2 is the enzyme responsible for occludin degradation under our experimental conditions. On the in vivo MCAO model, we also found that cerebral ischemia rapidly induced occludin degradation.

Rat Model of Middle Cerebral Artery Occlusion (MCAO)

The Laboratory Animal Care and Use Committee of the University of New Mexico approved all experimental protocols. Male Sprague Dawley rats (Charles River Laboratories) weighing 290-320 g were anesthetized with isoflurane (5% for induction, 2% for maintenance) in $N_2/O_2$ (70:30%) during surgical procedures and the body temperature was maintained at $37.5\pm0.5°$ C. using a heating pad. The rats were subjected to 1.5, 3, or 4.5 h of MCAO by using the intraluminal suture occlusion model, as we previously described [See e.g., Liu, W., et al., *Normobaric hyperoxia attenuates early blood-brain barrier disruption by inhibiting MMP-9-mediated occludin degradation in focal cerebral ischemia*. J Neurochem, 2009. 108(3): p. 811-20.]. Briefly, a 4-0 silicone-coated monofilament nylon suture was inserted into the internal carotid artery and advanced along the internal carotid artery to ~17-18 mm from the bifurcation, thereby blocking the ostium of the MCA. After MCAO, reperfusion was produced by gently withdrawing the suture, as we previously described. [See e.g., Liu, S., et al., *Electron paramagnetic resonance-guided normobaric hyperoxia treatment protects the brain by maintaining penumbral oxygenation in a rat model of transient focal cerebral ischemia*. J Cereb Blood Flow Metab, 2006. 26(10): p. 1274-84.]

Prior to reperfusion, all rats included in this study displayed neurologic deficit typical of MCAO, circling to the left (non-ischemic side).

Serum Biochemical Measurements

Before MCAO, blood sample was withdrawn from one side femoral vein and placed into serum tube. Right before reperfusion, another blood draw toke place at the other side femoral vein. Serum for protein level measurement was obtained by low speed centrifuge. Occludin (USCN, China), Claudin-5 (Biomatik, USA) and MMP-9 (R&D, USA) levels in serum were assayed by the ELISA kits, following the instruction, respectively.

Western Blot Analysis for Blood Occludin

Serum occludin was immunoprecipitated by a Dynabeads protein A immunoprecipition kit (Life technologies, USA) following the instruction. Briefly, 2 μg occludin antibody (Life technologies, USA) was connected to Dynabeads. After a wash, 100 μl serum was added to the Dynabeads-Ab complex. Following a thorough wash, occludin protein was eluted by SDS sample buffer at 70° C. for 10 min. Then, the sample was loaded in the Any kD Mini-PROTEAN TGX Gel (Bio-Rad, USA). After electrophorese, the protein in the gel was transferred onto PVDF membranes (Millipore). Membranes were blocked with Odyssey Blocking Buffer (Li-cor) and then incubated at 4° C. overnight with antibodies against occludin (diluted 1:250, Life technologies) followed by incubation with RDye 800CW goat anti-rabbit secondary antibodies (diluted 1:10,000, Li-cor) for 1 hr at room temperature. Immunoblots were photographed using the Odyssey® Infrared Imaging System (Li-cor) with Molecular Imaging Software V4.0.

Measurement of BBB Permeability

Before the 5 min reperfusion, 2% Evans blue in normal saline (3 mL/kg body weight) was injected into the femoral vein. At the end of the experiment, rats were deeply anesthetized with isoflurane and transcardially perfused with PBS till colorless fluid was obtained from the right atrium.

Brains were quickly taken out. To measure the amount of Evans blue dye in the brain, tissues from left or right hemisphere were separately homogenized in 1 mL 50% trichloroacetic acid. The fluorescence intensity of each collected supernatant was measured by Odyssey® Infrared Imaging System (Li-cor) with Molecular Imaging Software V4.0 (emission wavelength of 680 nm). The total Evan's blue content in each sample was calculated according to the external standard curve. The difference of dye content between ischemic and nonischemic hemispheric tissue reflected the extent of BBB damage.

Brain Tissue Collection

Rats were sacrificed by decapitation at the end of reperfusion. Brains were quickly removed and chilled in ice-cold PBS for 5 min. Brains were sectioned to 2-mm thick coronary slices, 2 mm away from the tip of the frontal lobe, which contained the main infarction area according to our earlier studies [See e.g., Liu, S., et al., *Interstitial pO2 in ischemic penumbra and core are differentially affected following transient focal cerebral ischemia in rats*. J Cereb Blood Flow Metab, 2004. 24(3): p. 343-9 and Yuan, Z., et al., *Normobaric hyperoxia delays and attenuates early nitric oxide production in focal cerebral ischemic rats*. Brain Res, 2010. 1352: p. 248-54.]

After digitally photographing the 2-mm thick brain slices, they were carefully cleaned of meninges, and then a longitudinal cut was made 2 mm away from the midline between two hemispheres to exclude tissue primarily supplied by the anterior cerebral artery. Nonischemic and ischemic hemispheric tissue was then collected from each brain slice, and freshly used for cerebral microvessel isolation.

Isolation of Cerebral Microvessels

Isolation of cerebral microvessels was performed after. The hemispheric brain tissue was minced and homogenized in 4 ml ice-cold PBS using a Dounce homogenizer. 50 μl homogenate (as brain tissue) was taken out for protein measurements. The rest homogenate was filtered through a 41-μm nylon mesh (Spectrum, Irving, Tex., USA), and the nylon mesh was washed three times with 5 ml PBS. Microvessels retained on the mesh were then washed off with PBS and pelleted by centrifugation at 4000 g for 10 min at 4° C. The pellets were collected as the cerebral microvessels and were stored at −80° C. until further analysis.

Western Blot Analysis for Occludin in Brain Tissue and Cerebral Microvessels

50 μl brain tissue was homogenized on ice in 200 μl RIPA buffer and cerebral microvessels were homogenized in 50 μl RIPA buffer. Homogenates were centrifuged at 16,000 g for 15 min at 4° C., and protein concentrations in supernatants were determined using protein assay reagents (Bio-Rad). After heating at 100° C. for 5 min, samples were electrophoretically separated on Any kD Mini-PROTEAN TGX Gel (Bio-Rad, USA) and transferred to PVDF membranes (Millipore). Membranes were blocked with Odyssey Blocking Buffer (Li-cor) and then incubated at 4° C. overnight with antibodies against occludin (diluted 1:250) or β-actin (diluted 1:2,000) followed by incubation with RDye 800CW goat anti-rabbit and IRDye 680 goat anti-mouse secondary antibodies (diluted 1:10,000, Li-cor) for 1 hr at room temperature. Immunoblots were photographed using the Odyssey® Infrared Imaging System (Li-cor) with Molecular Imaging Software V4.0.

Visualization of BBB Damage after Induced Ischemic Event

Figure 38:
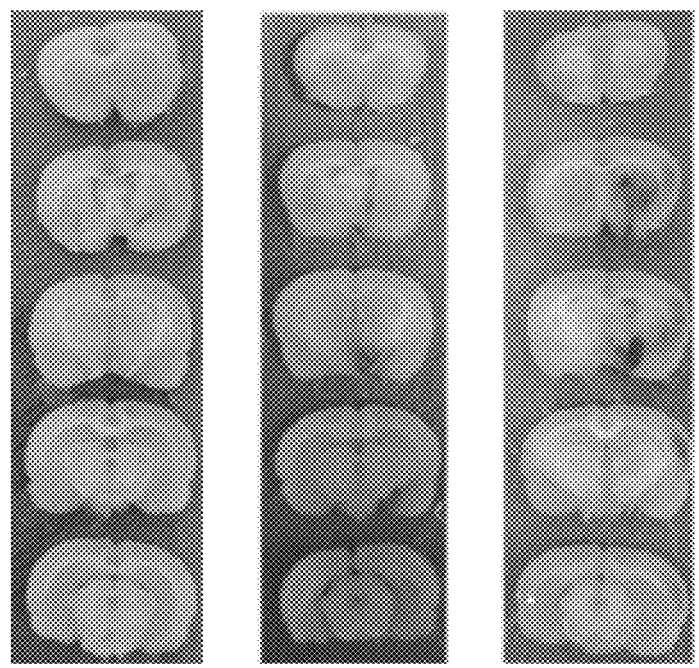
FIG. 38 shows the results of Evans Blue leakage tests on rat brains anfter an induced ischemic event.
Figure 39:
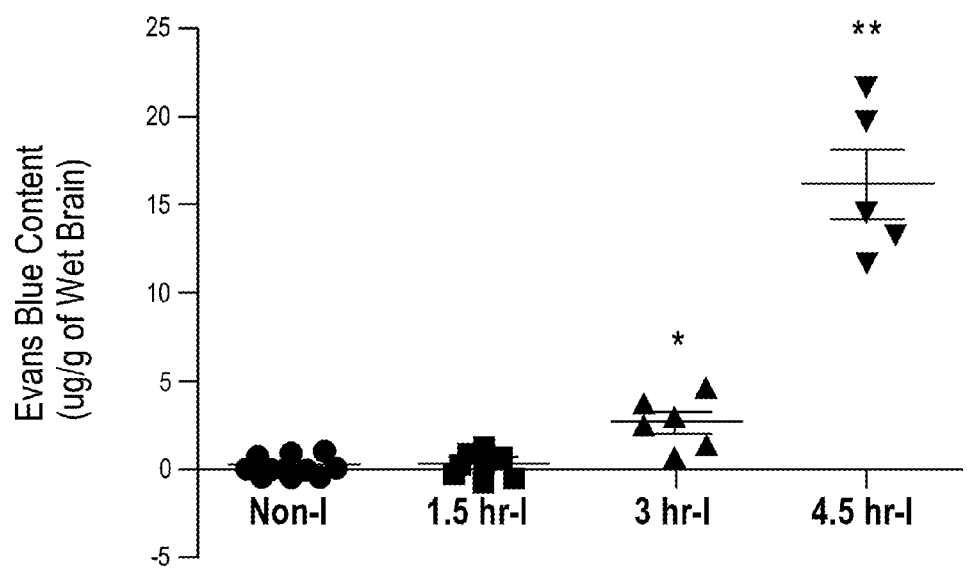
FIG. 39 shows the quantified data from the Evans Blue leakage tests of FIG. 38.

Evans blue leakage tests were performed on rat brain at different time intervals after induction of an ischemic event (MCAO). FIG. 38 shows the results of these tests. Evans blue is a large molecule dye that would not normally pass the blood brain barrier unless the barrier was disrupted. Accordingly, staining of the brain is a clear visual representation of both whether there has been disruption and the degree of disruption (greater staining indicates greater disruption.) As can clearly be seen in the photos, very little Evans blue is seen at the 1.5 hr time point. However, Evans blue starts to be visible at the 3 hr time point and, notably, evans Blue staining is easily detected by the 4.5 hr time point. dramatically increased Evans blue leakage. Data were presented as means±SE. *$p<0.05$,  $p<0.01$ versus 0 hr MCAO. This data is quantified in FIG. 39**.

Presence and Concentration of Occludin Fragments after Ischemic Event

Figure 40:
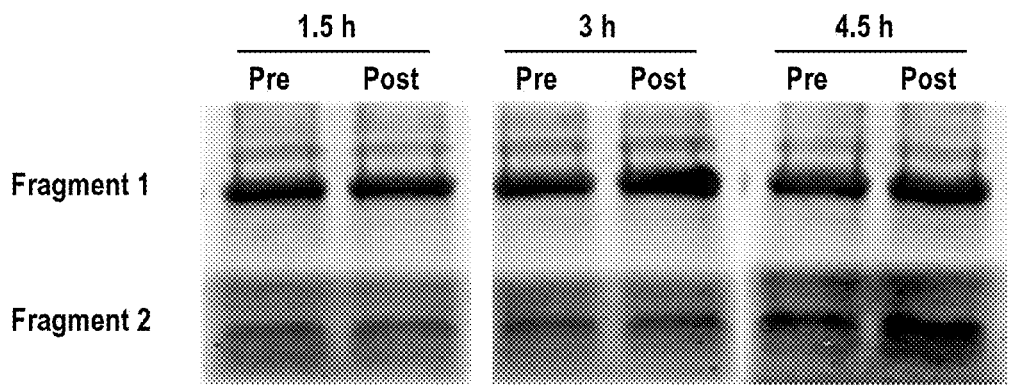
FIG. 40 shows gels from an ELISA assay for the presence and concentration of Occludin fragments 1 and 2 measured in blood collected from rats before and after MCAO.
Figure 42:
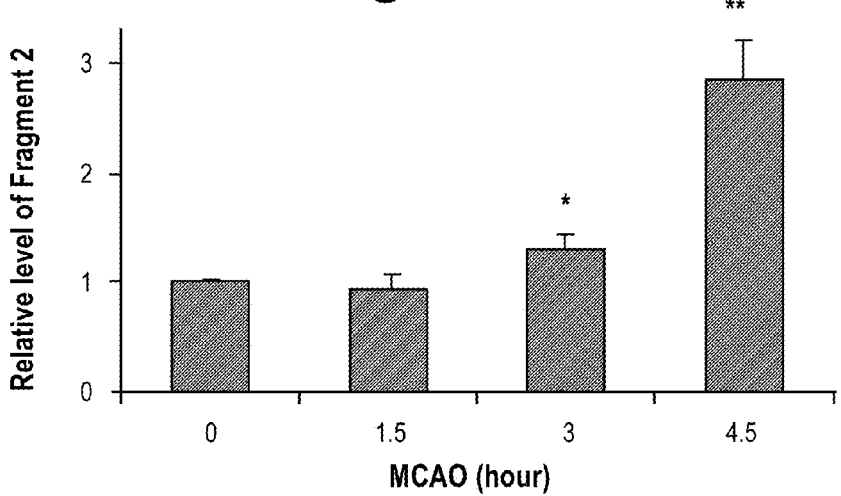
FIG. 42 is another graph showing quantified data from the ELISA assay.
Figure 43:
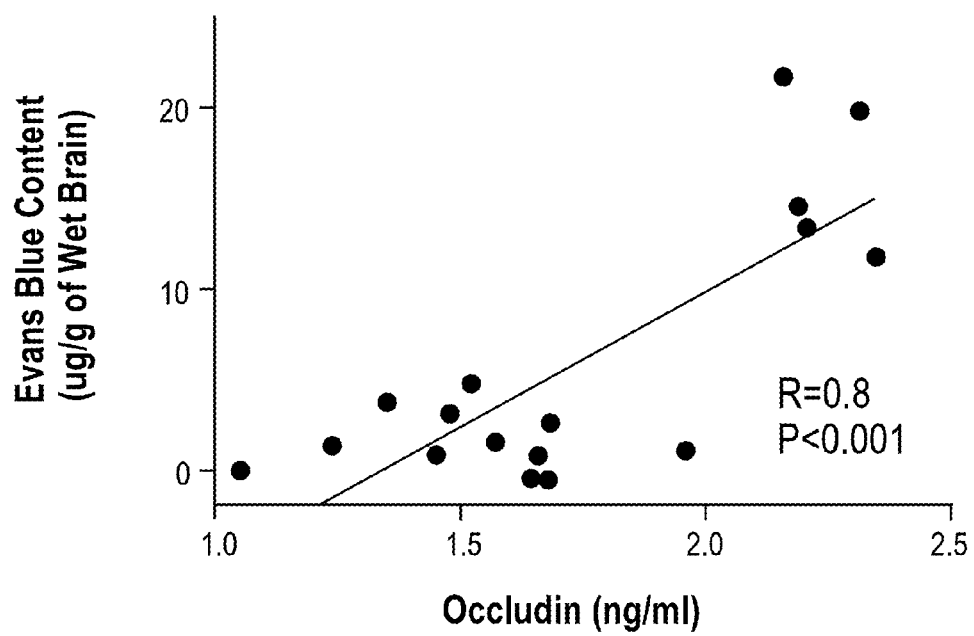
FIG. 43 is a plot showing a tight correlation between the concentration of occludin fragments in the blood and the degree of BBB disruption as measured above.
Figure 44:
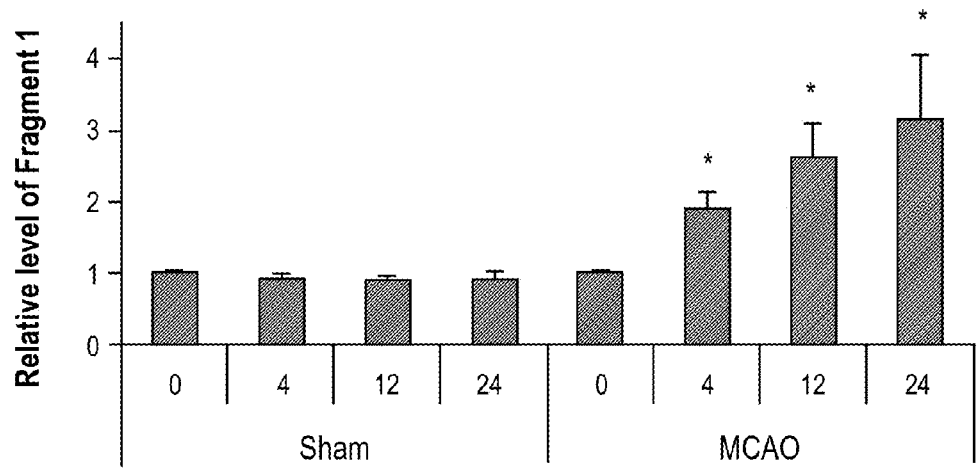
FIG. 44 extends the post-MCAO fragment 1 time point data from the experiments of FIG. 43 out to 24 hours.
Figure 45:
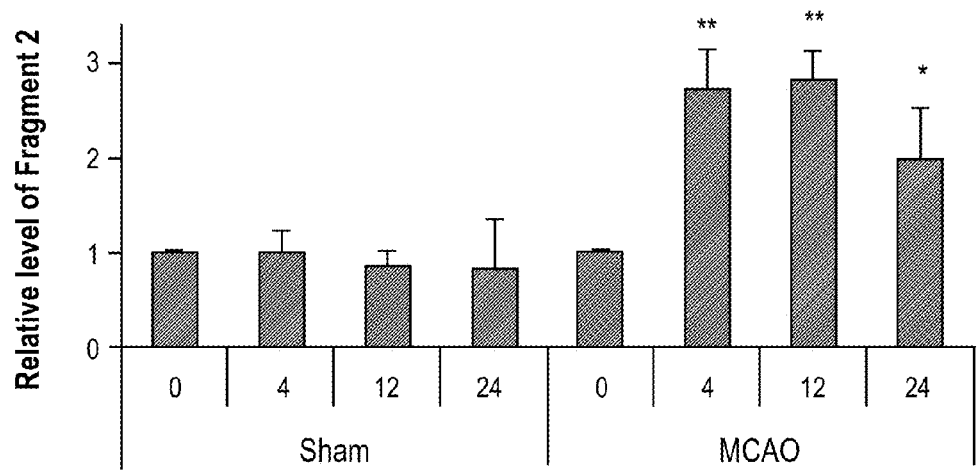
FIG. 45 extends the post-MCAO fragment 2 time point data from the experiments of FIG. 43 out to 24 hours.

The presence and concentration of Occludin fragments 1 and 2 was measured in blood collected from rats before and after MCAO. FIG. 40 shows the gels from the ELISA assay and FIGS. 41 and 42 are graphs showing the quantified data from these experiments. As shown fragment 1 shows a slow but gradual increase in concentration over time while fragment 2 increases sharply between the 3 and 4.5 hour time points. FIG. 43 is a plot showing a tight correlation between the concentration of occludin fragments in the blood and the degree of BBB disruption as measured above. FIGS. 44 and 45 extend the post-MCAO time points out to 24 hours. As shown, fragment 1 maintains the slow and deliberate upward trend while fragment 2 appears to peak between 4 and 12 hours and then decreases slightly, but does not return to baseline levels.

Figure 46:
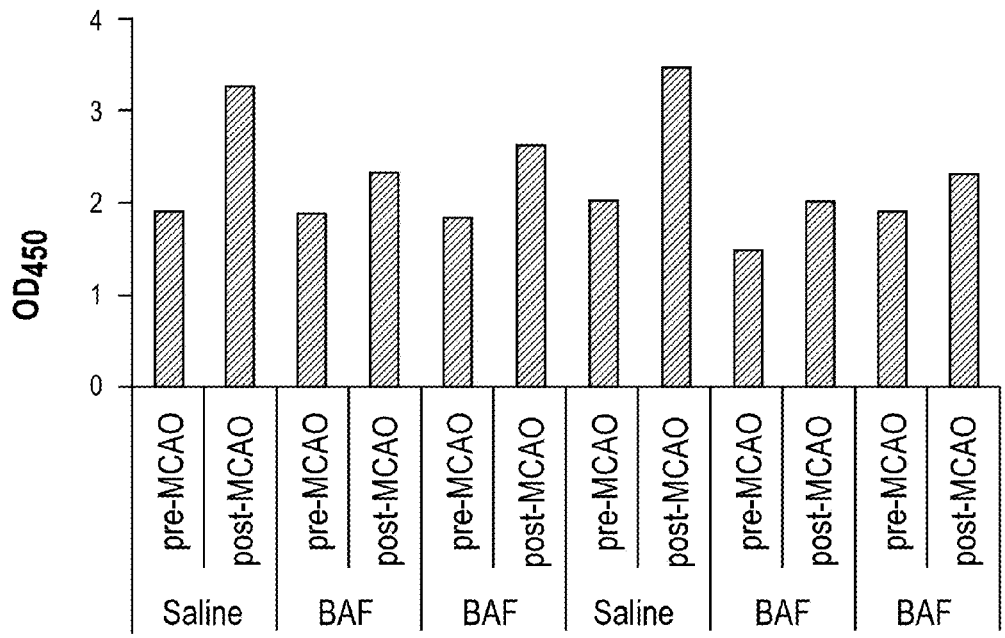
FIG. 46 is a graph showing the results of measurements (absorbance) of Occludin fragment 2 in blood collected from rats before and after stroke and with and without BAF treatment.
Figure 47:
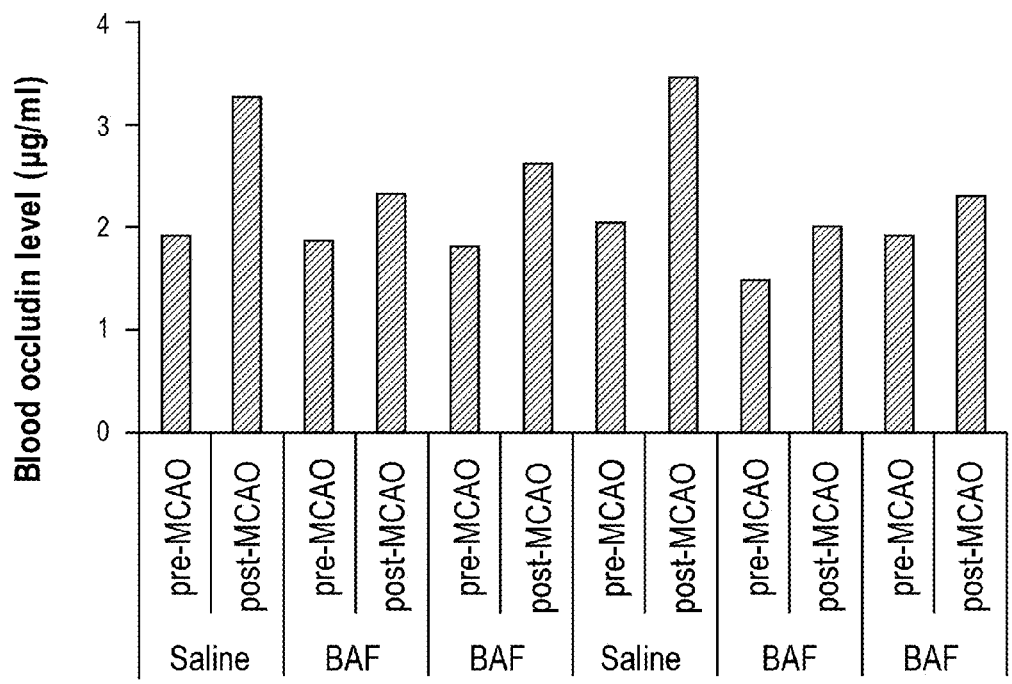
FIG. 47 is a graph showing the results of measurements of the concentration of Occludin fragment 2 in blood collected from rats before and after stroke and with and without BAF treatment.

Presence and Concentration of Occludin Fragment 2 after Ischemic Event with and without BAF Treatment The presence and concentration of Occludin fragment 2 was measured in blood collected from rats before and after stroke and with and without BAF treatment (BAF inhibits cleavage of occludin). FIGS. 46 and 47 are graphs showing the results (absorbance is shown in FIG. 46, while concentration is shown in FIG. 47). Increased concentrations of occludin fragment 2 are clearly seen in non-BAF treated rats after stroke. As expected, this increase was substantially lowered in BAF-treated rats.

Loss of Occludin in Brain and Microvessels

Figure 48:
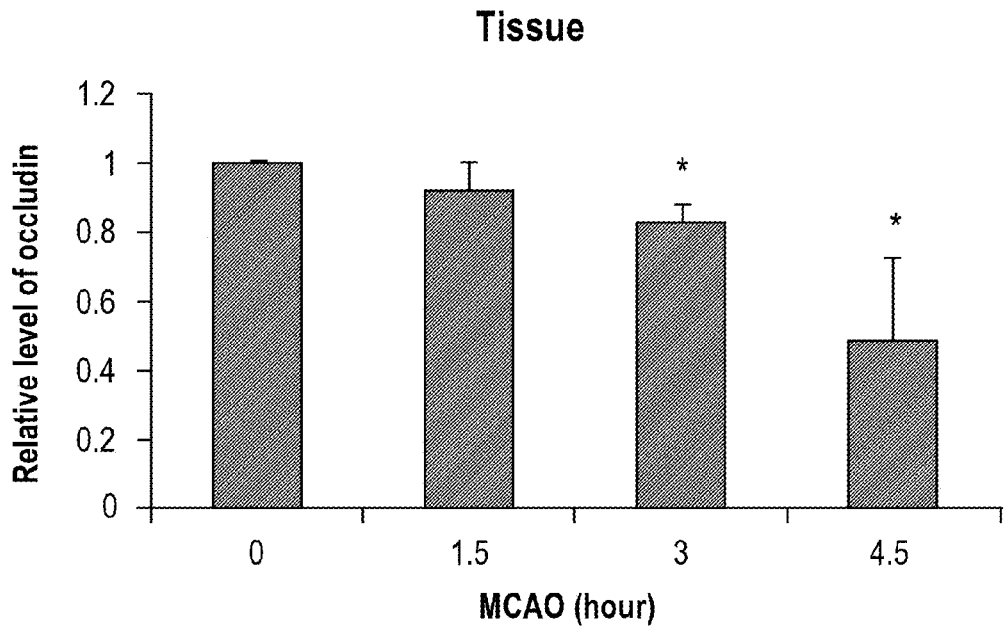
FIG. 48 is a graph showing the relative level of Occludin in brain tissue at various time points after MCAO.
Figure 49:
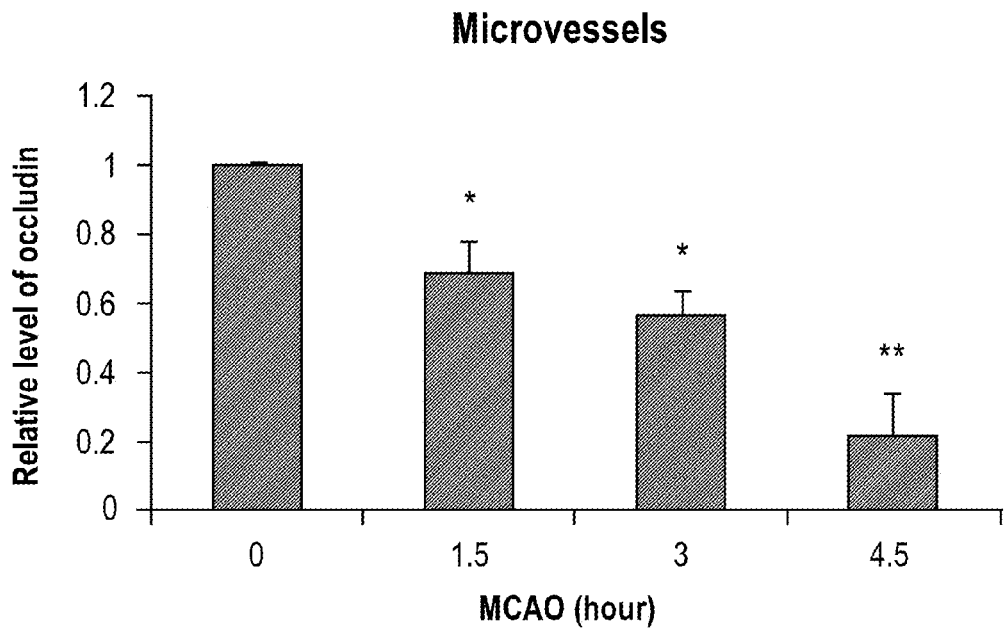
FIG. 49 is a graph showing the relative level of Occludin in brain-associated microvessels at various time points after MCAO.

FIGS. 48 and 49 show that occludin fragment 2 levels in the brain and microvessels clearly decrease over time after a stroke event, indicating that the occludin fragments detected in the experiments above originated in the brain and microvessels, as expected.

Detection of Claudin-5 and MMP-9 after Ischemic Event

Figure 50:
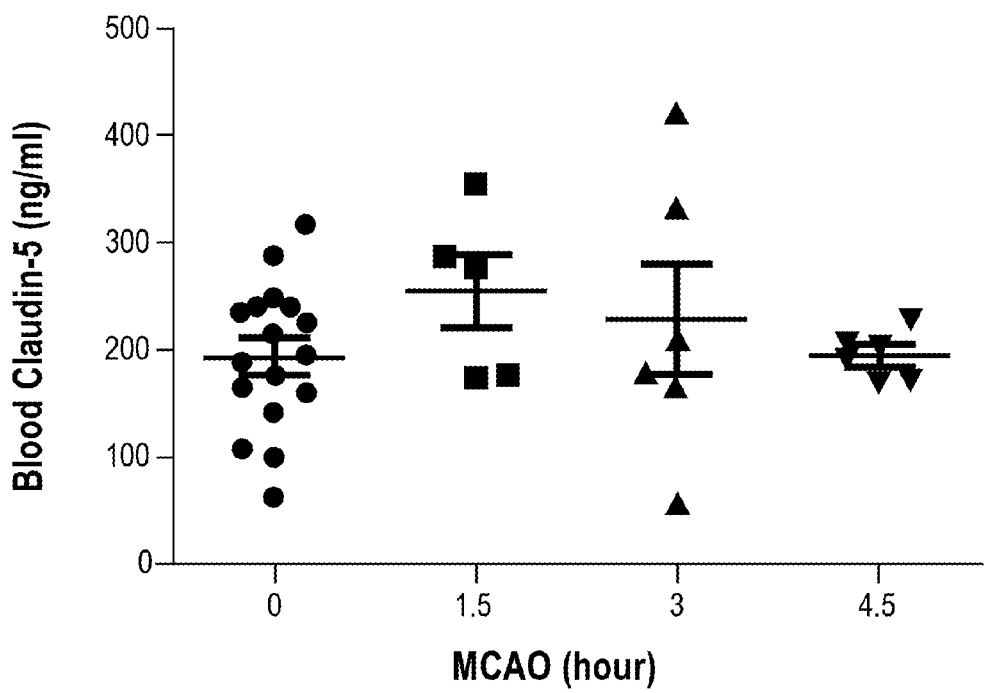
FIG. 50 shows the concentration of claudin-5 at various time points after MCAO.
Figure 51:
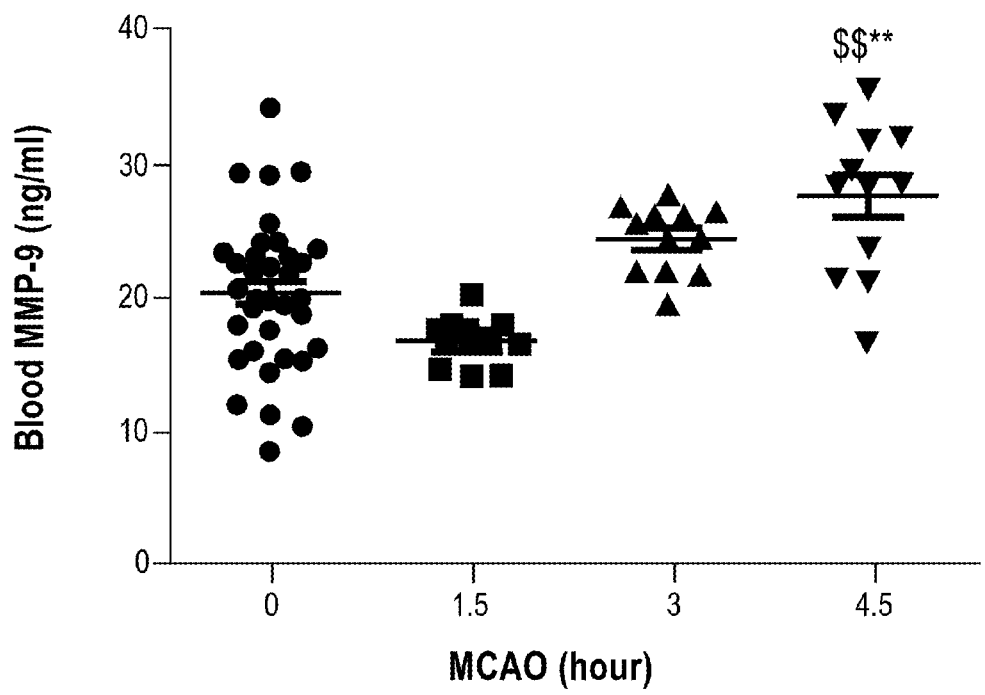
FIG. 51 shows the concentration of Blood MMP-9 levels at various time points after MCAO.

FIGS. 50 and 51 show the surprising results that the concentrations of claudin-5 and MMP-9, both tight junction proteins like occludin, do not significantly increase in concentration after an ischemic event. While a very slight increase might be seen in claudin-5, the increase is not statistically significant over the baseline.

REFERENCES

Alberts M J (1998) tPA in acute ischemic stroke: United States experience and issues for the future. Neurology 51:S53-55.

Andras I E, Pu H, Deli M A, Nath A, Hennig B, Toborek M (2003) HIV-1 Tat protein alters tight junction protein expression and distribution in cultured brain endothelial cells. J Neurosci Res 74:255-265.

Asahi M, Wang X, Mori T, Sumii T, Jung J C, Moskowitz M A, Fini M E, Lo E H (2001) Effects of matrix metalloproteinase-9 gene knock-out on the proteolysis of blood-brain barrier and white matter components after cerebral ischemia. J Neurosci 21:7724-7732.

Aviv R I, d'Esterre C D, Murphy B D, Hopyan J J, Buck B, Mallia G, Li V, Zhang L, Symons S P, Lee T Y (2009) Hemorrhagic transformation of ischemic stroke: prediction with CT perfusion. Radiology 250:867-877.

Bang O Y, Buck B H, Saver J L, Alger J R, Yoon S R, Starkman S, Ovbiagele B, Kim D, Ali L K, Sanossian N, Jahan R, Duckwiler G R, Vinuela F, Salamon N, Villablanca J P, Liebeskind D S (2007) Prediction of hemorrhagic transformation after recanalization therapy using T2*-permeability magnetic resonance imaging. Ann Neurol 62:170-176.

Benchenane K, Berezowski V, Fernandez-Monreal M, Brillault J, Valable S, Dehouck M P, Cecchelli R, Vivien D, Touzani O, Ali C (2005) Oxygen glucose deprivation switches the transport of tPA across the blood-brain barrier from an LRP-dependent to an increased LRP-independent process. Stroke 36:1065-1070.

Brown S, Bernardo M M, Li Z H, Kotra L P, Tanaka Y, Fridman R, Mobashery S, Sabatini D M (2000) Potent and selective mechanism-based inhibition of gelatinases. J Am Chem Soc 122:6799-6800.

Butcher S P, Bullock R, Graham D I, McCulloch J (1990) Correlation between amino acid release and neuropathologic outcome in rat brain following middle cerebral artery occlusion. Stroke 21:1727-1733.

Chen B, Friedman B, Cheng Q, Tsai P, Schim E, Kleinfeld D, Lyden P D (2009) Severe blood-brain barrier disruption and surrounding tissue injury. Stroke 40:e666-674.

Date I, Takagi N, Takagi K, Tanonaka K, Funakoshi H, Matsumoto K, Nakamura T, Takeo S (2006) Hepatocyte growth factor attenuates cerebral ischemia-induced increase in permeability of the blood-brain barrier and decreases in expression of tight junctional proteins in cerebral vessels. Neurosci Lett 407:141-145.

De Becker A, Van Hummelen P, Bakkus M, Vande Broek I, De Wever J, De Waele M, Van Riet I (2007) Migration of culture-expanded human mesenchymal stem cells through bone marrow endothelium is regulated by matrix metalloproteinase-2 and tissue inhibitor of metalloproteinase-3. Haematologica 92:440-449.

del Zoppo G J, von Kummer R, Hamann G F (1998) Ischaemic damage of brain microvessels: inherent risks for thrombolytic treatment in stroke. J Neurol Neurosurg Psychiatry 65:1-9.

Del Zoppo G J, Saver J L, Jauch E C, Adams H P, Jr. (2009) Expansion of the time window for treatment of acute ischemic stroke with intravenous tissue plasminogen activator: a science advisory from the American Heart Association/American Stroke Association. Stroke 40:2945-2948.

Derex L, Nighoghossian N (2008) Intracerebral haemorrhage after thrombolysis for acute ischaemic stroke: an update. J Neurol Neurosurg Psychiatry 79:1093-1099.

DiNapoli V A, Huber J D, Houser K, Li X, Rosen C L (2008) Early disruptions of the blood-brain barrier may contribute to exacerbated neuronal damage and prolonged functional recovery following stroke in aged rats. Neurobiol Aging 29:753-764.

Eckle T, Faigle M, Grenz A, Laucher S, Thompson L F, Eltzschig H K (2008) A2B adenosine receptor dampens hypoxia-induced vascular leak. Blood 111:2024-2035.

Elali A, Doeppner T R, Zechariah A, Hermann D M (2011) Increased Blood-Brain Barrier Permeability and Brain Edema After Focal Cerebral Ischemia Induced by Hyperlipidemia: Role of Lipid Peroxidation and Calpain-1/2, Matrix Metalloproteinase-2/9, and RhoA Overactivation. Stroke 42:3238-3244.

Ellison J A, Barone F C, Feuerstein G Z (1999) Matrix remodeling after stroke. De novo expression of matrix proteins and integrin receptors. Ann N Y Acad Sci 890:204-222.

Floyd R A (1999) Neuroinflammatory processes are important in neurodegenerative diseases: an hypothesis to explain the increased formation of reactive oxygen and nitrogen species as major factors involved in neurodegenerative disease development. Free Radic Biol Med 26:1346-1355.

Forster C (2008) Tight junctions and the modulation of barrier function in disease. Histochem Cell Biol 130:55-70.

Furuichi T, Liu W, Shi H, Miyake M, Liu K J (2005) Generation of hydrogen peroxide during brief oxygen-glucose deprivation induces preconditioning neuronal protection in primary cultured neurons. J Neurosci Res 79:816-824.

Gasche Y, Soccal P M, Kanemitsu M, Copin J C (2006) Matrix metalloproteinases and diseases of the central nervous system with a special emphasis on ischemic brain. Front Biosci 11:1289-1301.

Gerriets T, Walberer M, Ritschel N, Tschernatsch M, Mueller C, Bachmann G, Schoenburg M, Kaps M, Nedelmann M (2009) Edema formation in the hyperacute phase of ischemic stroke. Laboratory investigation. J Neurosurg 111:1036-1042.

Giebel S J, Menicucci G, McGuire P G, Das A (2005) Matrix metalloproteinases in early diabetic retinopathy and their role in alteration of the blood-retinal barrier. Lab Invest 85:597-607.

Gong Y, Hart E, Shchurin A, Hoover-Plow J (2008) Inflammatory macrophage migration requires MMP-9 activation by plasminogen in mice. J Clin Invest 118:3012-3024.

Grabovac V, Bernkop-Schnurch A (2006) Improvement of the intestinal membrane permeability of low molecular weight heparin by complexation with stem bromelain. International Journal of Pharmaceutics 326:153-159.

Hacke W, Kaste M, Bluhmki E, Brozman M, Davalos A, Guidetti D, Larrue V, Lees K R, Medeghri Z, Machnig T, Schneider D, von Kummer R, Wahlgren N, Toni D (2008) Thrombolysis with alteplase 3 to 4.5 hours after acute ischemic stroke. N Engl J Med 359:1317-1329.

Hallenbeck J M, Dutka A J (1990) Background review and current concepts of reperfusion injury. Arch Neurol 47:1245-1254.

Hawkins B T, Davis T P (2005) The blood-brain barrier/neurovascular unit in health and disease. Pharmacol Rev 57:173-185.

Heo J H, Lucero J, Abumiya T, Koziol J A, Copeland B R, del Zoppo G J (1999) Matrix metalloproteinases increase very early during experimental focal cerebral ischemia. J Cereb Blood Flow Metab 19:624-633.

Hjort N, Wu O, Ashkanian M, Soiling C, Mouridsen K, Christensen S, Gyldensted C, Andersen G, Ostergaard L (2008) MRI detection of early blood-brain barrier disruption: parenchymal enhancement predicts focal hemorrhagic transformation after thrombolysis. Stroke 39:1025-1028.

Jin R, Yang G, Li G (2010) Molecular insights and therapeutic targets for blood-brain barrier disruption in ischemic stroke: critical role of matrix metalloproteinases and tissue-type plasminogen activator. Neurobiol Dis 38:376-385.

Jung J E, Kim G S, Chen H, Maier C M, Narasimhan P, Song Y S, Niizuma K, Katsu M, Okami N, Yoshioka H, Sakata H, Goeders C E, Chan P H (2010) Reperfusion and neurovascular dysfunction in stroke: from basic mechanisms to potential strategies for neuroprotection. Molecular Neurobiology 41:172-179.

Kamada H, Yu F, Nito C, Chan P H (2007) Influence of hyperglycemia on oxidative stress and matrix metalloproteinase-9 activation after focal cerebral ischemia/reperfusion in rats: relation to blood-brain barrier dysfunction. Stroke 38:1044-1049.

Kassner A, Roberts T P, Moran B, Silver F L, Mikulis D J (2009) Recombinant tissue plasminogen activator increases blood-brain barrier disruption in acute ischemic stroke: an MR imaging permeability study. AJNR Am J Neuroradiol 30:1864-1869.

Kastrup A, Groschel K, Ringer T M, Redecker C, Cordesmeyer R, Witte O W, Terborg C (2008) Early disruption of the blood-brain barrier after thrombolytic therapy predicts hemorrhage in patients with acute stroke. Stroke 39:2385-2387.

Kolev K, Skopal J, Simon L, Csonka E, Machovich R, Nagy Z (2003) Matrix metalloproteinase-9 expression in post-hypoxic human brain capillary endothelial cells: H2O2 as a trigger and NF-kappaB as a signal transducer. Thromb Haemost 90:528-537.

Kondo N, Ogawa M, Wada H, Nishikawa S (2009) Thrombin induces rapid disassembly of claudin-5 from the tight junction of endothelial cells. Exp Cell Res 315:2879-2887.

Larson J, Schomberg S, Schroeder W, Carpenter T C (2008) Endothelial EphA receptor stimulation increases lung vascular permeability. Am J Physiol Lung Cell Mol Physiol 295:L431-439.

Latour L L, Kang D W, Ezzeddine M A, Chalela J A, Warach S (2004) Early blood-brain barrier disruption in human focal brain ischemia. Ann Neurol 56:468-477.

Lisanti M P, Scherer P E, Tang Z, Sargiacomo M (1994) Caveolae, caveolin and caveolin-rich membrane domains: a signalling hypothesis. Trends Cell Biol 4:231-235.

Lischper M, Beuck S, Thanabalasundaram G, Pieper C, Galla H J (2010) Metalloproteinase mediated occludin cleavage in the cerebral microcapillary endothelium under pathological conditions. Brain Res 1326:114-127.

Liu K J, Rosenberg G A (2005) Matrix metalloproteinases and free radicals in cerebral ischemia. Free Radic Biol Med 39:71-80.

Liu S, Liu M, Peterson S, Miyake M, Vallyathan V, Liu K J (2003) Hydroxyl radical formation is greater in striatal core than in penumbra in a rat model of ischemic stroke. J Neurosci Res 71:882-888.

Liu W, Hendren J, Qin X J, Liu K J (2009a) Normobaric hyperoxia reduces the neurovascular complications associated with delayed tissue plasminogen activator treatment in a rat model of focal cerebral ischemia. Stroke 40:2526-2531.

Liu W, Furuichi T, Miyake M, Rosenberg G A, Liu K J (2007) Differential expression of tissue inhibitor of metalloproteinases-3 in cultured astrocytes and neurons regulates the activation of matrix metalloproteinase-2. J Neurosci Res 85:829-836.

Liu W, Hendren J, Qin X J, Shen J, Liu K J (2009b) Normobaric hyperoxia attenuates early blood-brain barrier disruption by inhibiting MMP-9-mediated occludin degradation in focal cerebral ischemia. J Neurochem 108:811-820.

Liu W, Sood R, Chen Q, Sakoglu U, Hendren J, Cetin O, Miyake M, Liu K J (2008) Normobaric hyperoxia inhibits NADPH oxidase-mediated matrix metalloproteinase-9 induction in cerebral microvessels in experimental stroke. J Neurochem 107:1196-1205.

Lo A C, Chen A Y, Hung V K, Yaw L P, Fung M K, Ho M C, Tsang M C, Chung S S, Chung S K (2005) Endothelin-1 overexpression leads to further water accumulation and brain edema after middle cerebral artery occlusion via aquaporin 4 expression in astrocytic end-feet. J Cereb Blood Flow Metab 25:998-1011.

Mattila O S, Strbian D, Saksi J, Pikkarainen T O, Rantanen V, Tatlisumak T, Lindsberg P J (2011) Cerebral mast cells mediate blood-brain barrier disruption in acute experimental ischemic stroke through perivascular gelatinase activation. Stroke 42:3600-3605.

McCaffrey G, Staatz W D, Quigley C A, Nametz N, Seelbach M J, Campos C R, Brooks T A, Egleton R D, Davis T P (2007) Tight junctions contain oligomeric protein assembly critical for maintaining blood-brain barrier integrity in vivo. Journal of Neurochemistry 103:2540-2555.

McColl B W, Rothwell N J, Allan S M (2008) Systemic inflammation alters the kinetics of cerebrovascular tight junction disruption after experimental stroke in mice. J Neurosci 28:9451-9462.

Min D, Lyons J G, Jia J, Lo L, McLennan S V (2006) 2-Methoxy-2,4-diphenyl-3(2H)-furanone-labeled gelatin zymography and reverse zymography: a rapid real-time method for quantification of matrix metalloproteinases-2 and -9 and tissue inhibitors of metalloproteinases. Electrophoresis 27:357-364.

Nag S, Venugopalan R, Stewart D J (2007) Increased caveolin-1 expression precedes decreased expression of occludin and claudin-5 during blood-brain barrier breakdown. Acta Neuropathol 114:459-469.

Nagaraja T N, Ewing J R, Karki K, Jacobs P E, Divine G W, Fenstermacher J D, Patlak C S, Knight R A (2011) MRI and quantitative autoradiographic studies following bolus injections of unlabeled and (14) C-labeled gadolinium-diethylenetriaminepentaacetic acid in a rat model of stroke yield similar distribution volumes and blood-to-brain influx rate constants. NMR Biomed 24:547-558.

Nakamuta M, Kotoh K, Enjoji M, Nawata H (2005) Effects of fibril- or fixed-collagen on matrix metalloproteinase-1 and tissue inhibitor of matrix metalloproteinase-1 production in the human hepatocyte cell line HLE. World J Gastroenterol 11:2264-2268.

Nilsson U W, Dabrosin C (2006) Estradiol and tamoxifen regulate endostatin generation via matrix metalloproteinase activity in breast cancer in vivo. Cancer Res 66:4789-4794.

Okamoto T, Schlegel A, Scherer P E, Lisanti M P (1998) Caveolins, a family of scaffolding proteins for organizing "preassembled signaling complexes" at the plasma membrane. J Biol Chem 273:5419-5422.

Romanic A M, White R F, Arleth A J, Ohlstein E H, Barone F C (1998) Matrix metalloproteinase expression increases after cerebral focal ischemia in rats: inhibition of matrix metalloproteinase-9 reduces infarct size. Stroke 29:1020-1030.

Rosenberg G A, Mun-Bryce S (2004) Matrix metalloproteinases in neuroinflammation and cerebral ischemia. Ernst Schering Res Found Workshop:1-16.

Rosenberg G A, Estrada E Y, Dencoff J E (1998) Matrix metalloproteinases and TIMPs are associated with blood-brain barrier opening after reperfusion in rat brain. Stroke 29:2189-2195.

Sbai O, Ould-Yahoui A, Ferhat L, Gueye Y, Bernard A, Charrat E, Mehanna A, Risso J J, Chauvin J P, Fenouillet E, Rivera S, Khrestchatisky M (2010) Differential vesicular distribution and trafficking of MMP-2, MMP-9, and their inhibitors in astrocytes. Glia 58:344-366.

Sbai O, Ferhat L, Bernard A, Gueye Y, Ould-Yahoui A, Thiolloy S, Charrat E, Charton G, Tremblay E, Risso J J, Chauvin J P, Arsanto J P, Rivera S, Khrestchatisky M (2008) Vesicular trafficking and secretion of matrix metalloproteinases-2, -9 and tissue inhibitor of metalloproteinases-1 in neuronal cells. Mol Cell Neurosci 39:549-568.

Schnaeker E M, Ossig R, Ludwig T, Dreier R, Oberleithner H, Wilhelmi M, Schneider S W (2004) Microtubule-dependent matrix metalloproteinase-2/matrix metalloproteinase-9 exocytosis: prerequisite in human melanoma cell invasion. Cancer Res 64:8924-8931.

Simard J M, Kent T A, Chen M, Tarasov K V, Gerzanich V (2007) Brain oedema in focal ischaemia: molecular pathophysiology and theoretical implications. Lancet Neurol 6:258-268.

Slevin M, Krupinski J, Rovira N, Turu M, Luque A, Baldellou M, Sanfeliu C, de Vera N, Badimon L (2009) Identification of pro-angiogenic markers in blood vessels from stroked-affected brain tissue using laser-capture microdissection. BMC Genomics 10:113.

Smart E J, Graf G A, McNiven M A, Sessa W C, Engelman J A, Scherer P E, Okamoto T, Lisanti M P (1999) Caveolins, liquid-ordered domains, and signal transduction. Mol Cell Biol 19:7289-7304.

Song L, Ge S, Pachter J S (2007) Caveolin-1 regulates expression of junction-associated proteins in brain microvascular endothelial cells. Blood 109:1515-1523.

Stamatovic S M, Keep R F, Wang M M, Jankovic I, Andjelkovic A V (2009) Caveolae-mediated internalization of occludin and claudin-5 during CCL2-induced tight junction remodeling in brain endothelial cells. J Biol Chem 284:19053-19066.

Sun L, Zhou W, Mueller C, Sommer C, Heiland S, Bauer A T, Marti H H, Veltkamp R (2010) Oxygen therapy reduces secondary hemorrhage after thrombolysis in thromboembolic cerebral ischemia. J Cereb Blood Flow Metab 30:1651-1660.

Tanne D (2008) Imaging blood-brain barrier disruption: an evolving tool for assessing the risk of hemorrhage after thrombolysis. Nat Clin Pract Neurol 4:644-645.

Taraboletti G, D'Ascenzo S, Giusti I, Marchetti D, Borsotti P, Millimaggi D, Giavazzi R, Pavan A, Dolo V (2006) Bioavailability of VEGF in tumor-shed vesicles depends on vesicle burst induced by acidic pH. Neoplasia 8:96-103.

Vorbrodt A W, Dobrogowska D H (2004) Molecular anatomy of interendothelial junctions in human blood-brain barrier microvessels. Folia Histochem Cytobiol 42:67-75.

Wang X, Lo E H (2003) Triggers and mediators of hemorrhagic transformation in cerebral ischemia. Mol Neurobiol 28:229-244.

Wang X, Lee S R, Arai K, Lee S R, Tsuji K, Rebeck G W, Lo E H (2003) Lipoprotein receptor-mediated induction of matrix metalloproteinase by tissue plasminogen activator. Nat Med 9:1313-1317.

Wang Y, Zagorevski D V, Lennartz M R, Loegering D J, Stenken J A (2009) Detection of in vivo matrix metalloproteinase activity using microdialysis sampling and liquid chromatography/mass spectrometry. Anal Chem 81:9961-9971.

Wang Z, Leng Y, Tsai L K, Leeds P, Chuang D M (2011) Valproic acid attenuates blood-brain barrier disruption in a rat model of transient focal cerebral ischemia: the roles of HDAC and MMP-9 inhibition. J Cereb Blood Flow Metab 31:52-57.

Warach S, Latour L L (2004) Evidence of reperfusion injury, exacerbated by thrombolytic therapy, in human focal brain ischemia using a novel imaging marker of early blood-brain barrier disruption. Stroke 35:2659-2661.

Wen X, Li Y, Liu Y (2010) Opposite action of peroxisome proliferator-activated receptor-{gamma} in regulating renal inflammation: functional switch by its ligand. J Biol. Chem.

Wolburg H, Lippoldt A (2002) Tight junctions of the blood-brain barrier: development, composition and regulation. Vascul Pharmacol 38:323-337.

Yang M Z, Mun C H, Choi Y J, Baik J H, Park K A, Lee W T, Lee J E (2007a) Agmatine inhibits matrix metalloproteinase-9 via endothelial nitric oxide synthase in cerebral endothelial cells. Neurol Res 29:749-754.

Yang Y, Estrada E Y, Thompson J F, Liu W, Rosenberg G A (2007b) Matrix metalloproteinase-mediated disruption of tight junction proteins in cerebral vessels is reversed by synthetic matrix metalloproteinase inhibitor in focal ischemia in rat. J Cereb Blood Flow Metab 27:697-709.

Yepes M, Sandkvist M, Moore E G, Bugge T H, Strickland D K, Lawrence D A (2003) Tissue-type plasminogen activator induces opening of the blood-brain barrier via the LDL receptor-related protein. J Clin Invest 112:1533-1540.

Yong V W, Krekoski C A, Forsyth P A, Bell R, Edwards D R (1998) Matrix metalloproteinases and diseases of the CNS. Trends Neurosci 21:75-80.

Zehendner C M, Librizzi L, de Curtis M, Kuhlmann C R, Luhmann H J (2011) Caspase-3 contributes to ZO-1 and C1-5 tight-junction disruption in rapid anoxic neurovascular unit damage. PLoS One 6:e16760.

Zhang C, An J, Haile W B, Echeverry R, Strickland D K, Yepes M (2009) Microglial low-density lipoprotein receptor-related protein 1 mediates the effect of tissue-type plasminogen activator on matrix metalloproteinase-9 activity in the ischemic brain. J Cereb Blood Flow Metab 29:1946-1954.

Zhu D, Wang Y, Singh I, Bell R D, Deane R, Zhong Z, Sagare A, Winkler E A, Zlokovic B V (2010) Protein S controls hypoxic/ischemic blood-brain barrier disruption through the TAM receptor Tyro3 and sphingosine 1-phosphate receptor. Blood 115:4963-4972.

Zozulya A, Weidenfeller C, Galla H J (2008) Pericyte-endothelial cell interaction increases MMP-9 secretion at the blood-brain barrier in vitro. Brain Res 1189:1-11.

What is claimed is:

1. A method for determining whether the blood brain barrier of a patient has been disrupted, the method comprising:
   detecting cleaved occludin fragments comprising SEQ ID NO.: 19 in a blood sample obtained from the patient, wherein detecting cleaved occludin fragments comprises contacting at least a portion of the blood sample with an antibody that binds to a protein consisting of SEQ ID NO.: 19;
   determining the concentration of the cleaved occludin fragments in the patient's blood stream; and
   administering a dosage of tissue plasminogen activator (tPA) to the patient if the concentration of cleaved occluding fragments in the patient's blood stream is determined to be less than 2.0 µg/ml.

* * * * *

SEQUENCE LISTING

```
<160> NUMBER OF SEQ ID NOS: 19

<210> SEQ ID NO 1
<211> LENGTH: 54
<212> TYPE: PRT
<213> ORGANISM: Rat

<400> SEQUENCE: 1
```

Ser Thr Leu Ala Trp Asp Arg Ala Tyr Gly Thr Gly Ile Phe Gly Gly
1               5                   10                  15

Ser Met Asn Tyr Pro Tyr Gly Ser Gly Phe Gly Ser Tyr Gly Gly Gly
                20                  25                  30

Phe Gly Gly Tyr Gly Tyr Gly Tyr Gly Tyr Gly Tyr Gly Gly Tyr Thr
            35                  40                  45

Asp Pro Arg Ala Ala Lys
            50

<210> SEQ ID NO 2
<211> LENGTH: 44
<212> TYPE: PRT
<213> ORGANISM: Rat

<400> SEQUENCE: 2

Asn Pro Thr Ala Gln Ala Ser Gly Ser Met Tyr Gly Ser Gln Ile Tyr
1               5                   10                  15

Thr Ile Cys Ser Gln Phe Tyr Thr Pro Gly Gly Thr Gly Leu Tyr Val
                20                  25                  30

Asp Gln Tyr Leu Tyr His Tyr Cys Val Val Asp Pro
            35                  40

<210> SEQ ID NO 3
<211> LENGTH: 18
<212> TYPE: DNA
<213> ORGANISM: Mus musculus

<400> SEQUENCE: 3
taacctggat gccgtcgt                                                     18

<210> SEQ ID NO 4
<211> LENGTH: 21
<212> TYPE: DNA
<213> ORGANISM: Mus musculus

<400> SEQUENCE: 4
ttcaggtaat aagcaccctt g                                                 21

<210> SEQ ID NO 5
<211> LENGTH: 19
<212> TYPE: DNA
<213> ORGANISM: Mus musculus

<400> SEQUENCE: 5
acgacataga cggcatcca                                                    19

<210> SEQ ID NO 6
<211> LENGTH: 20
<212> TYPE: DNA
<213> ORGANISM: Mus musculus

<400> SEQUENCE: 6
gctgtggttc agttgtggtg                                                   20

<210> SEQ ID NO 7
<211> LENGTH: 21
<212> TYPE: DNA
<213> ORGANISM: Mus musculus

<400> SEQUENCE: 7
caatgtgtcc gtcgtggatc t                                                 21

<210> SEQ ID NO 8
<211> LENGTH: 22
<212> TYPE: DNA
<213> ORGANISM: Mus musculus

<400> SEQUENCE: 8
gtcctcagtg tagcccaaga tg                                            22

<210> SEQ ID NO 9
<211> LENGTH: 24
<212> TYPE: DNA
<213> ORGANISM: Rattus norvegicus

<400> SEQUENCE: 9
gatctgcaag caagacattg tctt                                          24

<210> SEQ ID NO 10
<211> LENGTH: 22
<212> TYPE: DNA
<213> ORGANISM: Rattus norvegicus

<400> SEQUENCE: 10
gccaaataaa ccgatccttg aa                                            22

<210> SEQ ID NO 11
<211> LENGTH: 21
<212> TYPE: DNA
<213> ORGANISM: Rattus norvegicus

<400> SEQUENCE: 11
gtaaccctgg tcaccggact t                                             21

<210> SEQ ID NO 12
<211> LENGTH: 20
<212> TYPE: DNA
<213> ORGANISM: Rattus norvegicus

<400> SEQUENCE: 12
atacgttccc ggctgatcag                                               20

<210> SEQ ID NO 13
<211> LENGTH: 20
<212> TYPE: DNA
<213> ORGANISM: Rattus norvegicus

<400> SEQUENCE: 13
agacctgaat gtgaaggaag                                               20

<210> SEQ ID NO 14
<211> LENGTH: 21
<212> TYPE: DNA
<213> ORGANISM: Rattus norvegicus

<400> SEQUENCE: 14
ccttgggatt ggtgactctg a                                             21

<210> SEQ ID NO 15
<211> LENGTH: 12
<212> TYPE: PRT
<213> ORGANISM: Rat

<400> SEQUENCE: 15

```
Asp Tyr Val Glu Arg Val Asp Ser Pro Met Ala Tyr
1               5                  10
```

<210> SEQ ID NO 16
<211> LENGTH: 522
<212> TYPE: PRT
<213> ORGANISM: Homo Sapiens

<400> SEQUENCE: 16

```
Met Ser Ser Arg Pro Leu Glu Ser Pro Pro Tyr Arg Pro Asp Glu
1               5                   10                  15

Phe Lys Pro Asn His Tyr Ala Pro Ser Asn Asp Ile Tyr Gly Gly Glu
                20                  25                  30

Met His Val Arg Pro Met Leu Ser Gln Pro Ala Tyr Ser Phe Tyr Pro
            35                  40                  45

Glu Asp Glu Ile Leu His Phe Tyr Lys Trp Thr Ser Pro Pro Gly Val
50                  55                  60

Ile Arg Ile Leu Ser Met Leu Ile Ile Val Met Cys Ile Ala Ile Phe
65                  70                  75                  80

Ala Cys Val Ala Ser Thr Leu Ala Trp Asp Arg Gly Tyr Gly Thr Ser
                85                  90                  95

Leu Leu Gly Gly Ser Val Gly Tyr Pro Tyr Gly Ser Gly Phe Gly
                100                 105                 110

Ser Tyr Gly Ser Gly Tyr Gly Tyr Gly Tyr Gly Tyr Gly Tyr
                115                 120                 125

Gly Gly Tyr Thr Asp Pro Arg Ala Ala Lys Gly Phe Met Leu Ala Met
            130                 135                 140

Ala Ala Phe Cys Phe Ile Ala Ala Leu Val Ile Phe Val Thr Ser Val
145                 150                 155                 160

Ile Arg Ser Glu Met Ser Arg Thr Arg Tyr Tyr Leu Ser Val Ile
                165                 170                 175

Ile Val Ser Ala Ile Leu Gly Ile Met Val Phe Ile Ala Thr Ile Val
                180                 185                 190

Tyr Ile Met Gly Val Asn Pro Thr Ala Gln Ser Ser Gly Ser Leu Tyr
                195                 200                 205

Gly Ser Gln Ile Tyr Ala Leu Cys Asn Gln Phe Tyr Thr Pro Ala Ala
                210                 215                 220

Thr Gly Leu Tyr Val Asp Gln Tyr Leu Tyr His Tyr Cys Val Val Asp
225                 230                 235                 240

Pro Gln Glu Ala Ile Ala Ile Val Leu Gly Phe Met Ile Ile Val Ala
                245                 250                 255

Phe Ala Leu Ile Ile Phe Phe Ala Val Lys Thr Arg Arg Lys Met Asp
                260                 265                 270

Arg Tyr Asp Lys Ser Asn Ile Leu Trp Asp Lys Glu His Ile Tyr Asp
                275                 280                 285

Glu Gln Pro Pro Asn Val Glu Glu Trp Val Lys Asn Val Ser Ala Gly
                290                 295                 300

Thr Gln Asp Val Pro Ser Pro Ser Asp Tyr Val Glu Arg Val Asp
305                 310                 315                 320

Ser Pro Met Ala Tyr Ser Ser Asn Gly Lys Val Asn Asp Lys Arg Phe
                325                 330                 335

Tyr Pro Glu Ser Ser Tyr Lys Ser Thr Pro Val Pro Glu Val Val Gln
                340                 345                 350

Glu Leu Pro Leu Thr Ser Pro Val Asp Asp Phe Arg Gln Pro Arg Tyr
                355                 360                 365
```

```
Ser Ser Gly Gly Asn Phe Glu Thr Pro Ser Lys Arg Ala Pro Ala Lys
    370                 375                 380

Gly Arg Ala Gly Arg Ser Lys Arg Thr Glu Gln Asp His Tyr Glu Thr
385                 390                 395                 400

Asp Tyr Thr Thr Gly Gly Glu Ser Cys Asp Glu Leu Glu Glu Asp Trp
                405                 410                 415

Ile Arg Glu Tyr Pro Pro Ile Thr Ser Asp Gln Gln Arg Gln Leu Tyr
            420                 425                 430

Lys Arg Asn Phe Asp Thr Gly Leu Gln Glu Tyr Lys Ser Leu Gln Ser
        435                 440                 445

Glu Leu Asp Glu Ile Asn Lys Glu Leu Ser Arg Leu Asp Lys Glu Leu
    450                 455                 460

Asp Asp Tyr Arg Glu Glu Ser Glu Glu Tyr Met Ala Ala Ala Asp Glu
465                 470                 475                 480

Tyr Asn Arg Leu Lys Gln Val Lys Gly Ser Ala Asp Tyr Lys Ser Lys
                485                 490                 495

Lys Asn His Cys Lys Gln Leu Lys Ser Lys Leu Ser His Ile Lys Lys
            500                 505                 510

Met Val Gly Asp Tyr Asp Arg Gln Lys Thr
            515                 520

<210> SEQ ID NO 17
<211> LENGTH: 523
<212> TYPE: PRT
<213> ORGANISM: Rattus norvegicus

<400> SEQUENCE: 17

Met Ser Val Arg Pro Phe Glu Ser Pro Pro Tyr Arg Pro Asp Glu
1               5                   10                  15

Phe Lys Pro Asn His Tyr Ala Pro Ser Asn Asp Met Tyr Gly Gly Glu
                20                  25                  30

Met His Val Arg Pro Met Leu Ser Gln Pro Ala Tyr Ser Phe Tyr Pro
            35                  40                  45

Glu Asp Glu Ile Leu His Phe Tyr Lys Trp Thr Ser Pro Pro Gly Val
    50                  55                  60

Ile Arg Ile Leu Ser Met Leu Val Ile Met Cys Ile Ala Val Phe
65                  70                  75                  80

Ala Cys Val Ala Ser Thr Leu Ala Trp Asp Arg Ala Tyr Gly Thr Gly
                85                  90                  95

Ile Phe Gly Gly Ser Met Asn Tyr Pro Tyr Gly Ser Gly Phe Gly Ser
            100                 105                 110

Tyr Gly Gly Gly Phe Gly Gly Tyr Gly Tyr Gly Tyr Gly Tyr
        115                 120                 125

Gly Gly Tyr Thr Asp Pro Arg Ala Ala Lys Gly Phe Leu Leu Ala Met
    130                 135                 140

Ala Ala Phe Cys Phe Ile Ala Ser Leu Val Ile Phe Val Thr Ser Val
145                 150                 155                 160

Ile Arg Ser Gly Met Ser Arg Thr Arg Arg Tyr Tyr Leu Ile Val Ile
                165                 170                 175

Ile Val Ser Ala Ile Leu Gly Ile Met Val Phe Ile Ala Thr Ile Val
            180                 185                 190

Tyr Ile Met Gly Val Asn Pro Thr Ala Gln Ala Ser Gly Ser Met Tyr
        195                 200                 205

Gly Ser Gln Ile Tyr Thr Ile Cys Ser Gln Phe Tyr Thr Pro Gly Gly
```

```
                       210                 215                 220
Thr Gly Leu Tyr Val Asp Gln Tyr Leu Tyr His Tyr Cys Val Val Asp
225                 230                 235                 240

Pro Gln Glu Ala Ile Ala Ile Val Leu Gly Phe Met Ile Ile Val Ala
                    245                 250                 255

Phe Ala Leu Ile Ile Val Phe Ala Val Lys Thr Arg Arg Lys Met Asp
                260                 265                 270

Arg Tyr Asp Lys Ser Asn Ile Leu Trp Asp Lys Glu His Ile Tyr Asp
            275                 280                 285

Glu Gln Pro Pro Asn Val Glu Glu Trp Val Lys Asn Val Ser Ala Gly
        290                 295                 300

Thr Gln Asp Met Pro Pro Pro Ser Asp Tyr Ala Glu Arg Val Asp
305                 310                 315                 320

Ser Pro Met Ala Tyr Ser Ser Asn Gly Lys Val Asn Gly Lys Arg Ser
                    325                 330                 335

Tyr Pro Asp Ser Leu Tyr Lys Ser Pro Pro Leu Val Pro Glu Val Ala
                340                 345                 350

Gln Glu Ile Pro Leu Thr Leu Ser Val Asp Asp Phe Arg Gln Pro Arg
            355                 360                 365

Tyr Ser Ser Asn Asp Asn Leu Glu Thr Pro Ser Lys Arg Thr Pro Thr
        370                 375                 380

Lys Gly Lys Ala Gly Lys Ala Lys Arg Thr Asp Pro Asp His Tyr Glu
385                 390                 395                 400

Thr Asp Tyr Thr Thr Gly Gly Glu Ser Cys Asp Glu Leu Glu Glu Asp
                    405                 410                 415

Trp Leu Arg Glu Tyr Pro Pro Ile Thr Ser Asp Gln Gln Arg Gln Leu
                420                 425                 430

Tyr Lys Arg Asn Phe Asp Ala Gly Leu Gln Glu Tyr Lys Ser Leu Leu
            435                 440                 445

Ala Glu Leu Asp Glu Val Asn Lys Glu Leu Ser Arg Leu Asp Arg Glu
        450                 455                 460

Leu Asp Asp Tyr Arg Glu Glu Ser Glu Glu Tyr Met Ala Ala Ala Asp
465                 470                 475                 480

Glu Tyr Asn Arg Leu Lys Gln Val Lys Gly Ser Ala Asp Tyr Lys Ser
                    485                 490                 495

Lys Lys Asn Tyr Cys Lys Gln Leu Lys Ser Lys Leu Ser His Ile Lys
            500                 505                 510

Arg Met Val Gly Asp Tyr Asp Arg Arg Lys Thr
            515                 520

<210> SEQ ID NO 18
<211> LENGTH: 403
<212> TYPE: PRT
<213> ORGANISM: Rattus norvegicus

<400> SEQUENCE: 18

Gly Tyr Gly Tyr Gly Tyr Gly Tyr Gly Tyr Thr Asp Pro Arg Ala
1               5                   10                  15

Ala Lys Gly Phe Leu Leu Ala Met Ala Ala Phe Cys Phe Ile Ala Ser
                20                  25                  30

Leu Val Ile Phe Val Thr Ser Val Ile Arg Ser Gly Met Ser Arg Thr
            35                  40                  45

Arg Arg Tyr Tyr Leu Ile Val Ile Val Ser Ala Ile Leu Gly Ile
        50                  55                  60
```

```
Met Val Phe Ile Ala Thr Ile Val Tyr Ile Met Gly Val Asn Pro Thr
 65                  70                  75                  80

Ala Gln Ala Ser Gly Ser Met Tyr Gly Ser Gln Ile Tyr Thr Ile Cys
                 85                  90                  95

Ser Gln Phe Tyr Thr Pro Gly Gly Thr Gly Leu Tyr Val Asp Gln Tyr
            100                 105                 110

Leu Tyr His Tyr Cys Val Val Asp Pro Gln Glu Ala Ile Ala Ile Val
        115                 120                 125

Leu Gly Phe Met Ile Ile Val Ala Phe Ala Leu Ile Ile Val Phe Ala
130                 135                 140

Val Lys Thr Arg Arg Lys Met Asp Arg Tyr Asp Lys Ser Asn Ile Leu
145                 150                 155                 160

Trp Asp Lys Glu His Ile Tyr Asp Glu Gln Pro Pro Asn Val Glu Glu
                165                 170                 175

Trp Val Lys Asn Val Ser Ala Gly Thr Gln Asp Met Pro Pro Pro Pro
            180                 185                 190

Ser Asp Tyr Ala Glu Arg Val Asp Ser Pro Met Ala Tyr Ser Ser Asn
        195                 200                 205

Gly Lys Val Asn Gly Lys Arg Ser Tyr Pro Asp Ser Leu Tyr Lys Ser
210                 215                 220

Pro Pro Leu Val Pro Glu Val Ala Gln Glu Ile Pro Leu Thr Leu Ser
225                 230                 235                 240

Val Asp Asp Phe Arg Gln Pro Arg Tyr Ser Asn Asp Asn Leu Glu
                245                 250                 255

Thr Pro Ser Lys Arg Thr Pro Thr Lys Gly Lys Ala Gly Lys Ala Lys
            260                 265                 270

Arg Thr Asp Pro Asp His Tyr Glu Thr Asp Tyr Thr Thr Gly Gly Glu
        275                 280                 285

Ser Cys Asp Glu Leu Glu Asp Trp Leu Arg Glu Tyr Pro Pro Ile
        290                 295                 300

Thr Ser Asp Gln Gln Arg Gln Leu Tyr Lys Arg Asn Phe Asp Ala Gly
305                 310                 315                 320

Leu Gln Glu Tyr Lys Ser Leu Leu Ala Glu Leu Asp Glu Val Asn Lys
                325                 330                 335

Glu Leu Ser Arg Leu Asp Arg Glu Leu Asp Asp Tyr Arg Glu Glu Ser
            340                 345                 350

Glu Glu Tyr Met Ala Ala Ala Asp Glu Tyr Asn Arg Leu Lys Gln Val
        355                 360                 365

Lys Gly Ser Ala Asp Tyr Lys Ser Lys Lys Asn Tyr Cys Lys Gln Leu
370                 375                 380

Lys Ser Lys Leu Ser His Ile Lys Arg Met Val Gly Asp Tyr Asp Arg
385                 390                 395                 400

Arg Lys Thr

<210> SEQ ID NO 19
<211> LENGTH: 203
<212> TYPE: PRT
<213> ORGANISM: Rattus norvegicus

<400> SEQUENCE: 19

Ser Pro Met Ala Tyr Ser Ser Asn Gly Lys Val Asn Gly Lys Arg Ser
 1               5                  10                  15

Tyr Pro Asp Ser Leu Tyr Lys Ser Pro Pro Leu Val Pro Glu Val Ala
                20                  25                  30
```

```
Gln Glu Ile Pro Leu Thr Leu Ser Val Asp Asp Phe Arg Gln Pro Arg
            35                  40                  45

Tyr Ser Ser Asn Asp Asn Leu Glu Thr Pro Ser Lys Arg Thr Pro Thr
    50                  55                  60

Lys Gly Lys Ala Gly Lys Ala Lys Arg Thr Asp Pro Asp His Tyr Glu
65                  70                  75                  80

Thr Asp Tyr Thr Thr Gly Gly Glu Ser Cys Asp Glu Leu Glu Glu Asp
                85                  90                  95

Trp Leu Arg Glu Tyr Pro Pro Ile Thr Ser Asp Gln Gln Arg Gln Leu
            100                 105                 110

Tyr Lys Arg Asn Phe Asp Ala Gly Leu Gln Glu Tyr Lys Ser Leu Leu
            115                 120                 125

Ala Glu Leu Asp Glu Val Asn Lys Glu Leu Ser Arg Leu Asp Arg Glu
    130                 135                 140

Leu Asp Asp Tyr Arg Glu Glu Ser Glu Glu Tyr Met Ala Ala Ala Asp
145                 150                 155                 160

Glu Tyr Asn Arg Leu Lys Gln Val Lys Gly Ser Ala Asp Tyr Lys Ser
                165                 170                 175

Lys Lys Asn Tyr Cys Lys Gln Leu Lys Ser Lys Leu Ser His Ile Lys
            180                 185                 190

Arg Met Val Gly Asp Tyr Asp Arg Arg Lys Thr
            195                 200
```